United States Patent [19]

Epstein et al.

[11] Patent Number: 5,482,971
[45] Date of Patent: Jan. 9, 1996

[54] BETA$_3$-ADRENERGIC AGENTS AND THEIR USE IN PHARMACEUTICAL COMPOSITIONS

[75] Inventors: Joseph W. Epstein; Gary H. Birnberg, both of Monroe; Feng L. Qing, Pearl River, all of N.Y.

[73] Assignee: American Cyanamid Company, Pearl River, N.Y.

[21] Appl. No.: 130,601

[22] Filed: Oct. 1, 1993

[51] Int. Cl.$^6$ ............... A61K 31/335; C07D 317/46
[52] U.S. Cl. ............ 514/465; 514/466; 514/450; 514/452; 549/362; 549/436; 549/437; 549/438; 549/441; 549/443
[58] Field of Search .................. 549/436, 437, 549/438, 441, 443, 362; 514/465, 466, 450, 452

[56] References Cited

U.S. PATENT DOCUMENTS 4,751,246  6/1988  Philion ............... 564/344
5,106,867  4/1992  Blum et al. ........... 549/437

FOREIGN PATENT DOCUMENTS 516349   12/1992  European Pat. Off. .
2834107  2/1979   Germany .
3003505  8/1980   Germany .

OTHER PUBLICATIONS

Simiand et al, Antidepressant Profile in rodents of SR58611A, European Journal, 219(1992), 193–201.

*Primary Examiner*—Bernard Dentz
*Attorney, Agent, or Firm*—Hedman, Gibson & Costigan

[57] ABSTRACT

This invention is concerned with novel compounds of formula I:

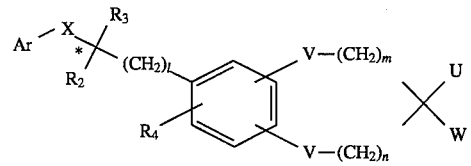

which are selective beta$_3$-adrenergic agents.

17 Claims, No Drawings

BETA₃-ADRENERGIC AGENTS AND THEIR USE IN PHARMACEUTICAL COMPOSITIONS

BACKGROUND OF THE INVENTION

It is well known to employ medicinal agents in the treatment of persons suffering from diabetes, hyperglycemia and obesity.

Bloom et al., U.S. Pat. No. 5,061,727, discloses compounds having the general formula:

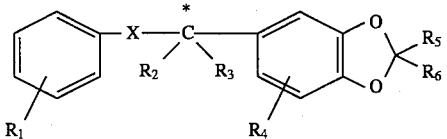

wherein $R_1$ and $R_4$ are independently hydrogen, $(C_1-C_4)$alkyl, $(C_1-C_4)$alkoxy, hydroxy, halogen, trifluoromethyl, carboxy, hydroxyalkyl, alkoxycarbonyl, $(C_1-C_4)$ thioalkyl, sulfonyl or sulfinyl;

X is a divalent radical:

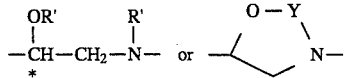

wherein R' is hydrogen, $(C_1-C_4)$alkyl, or $(C_1-C_4)$acyl;

Y is carbonyl or thiocarbonyl;

$R_2$ and $R_3$ are independently hydrogen or $(C_1-C_4)$alkyl;

$R_5$ and $R_6$ are independently hydrogen, carboxy, alkoxycarbonyl, hydroxymethyl, —CH₂OCH₂COOR₇ or —CH₂OCH₂CH₂OR₇, wherein $R_7$ is hydrogen or $(C_1-C_4)$alkyl;

with the proviso that $R_5$ and $R_6$ may not both be hydrogen; which are useful in the treatment of diabetes, hyperglycemia and obesity; and which show a greater degree of selectivity for the beta₃-adrenergic receptor than reference agents cited within the patent.

SUMMARY OF THE INVENTION

This invention is concerned with novel compounds of formula I:

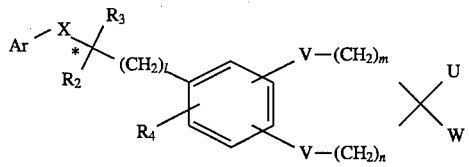

wherein:

Ar is naphth-(1 or 2)-yl —[wherein the substitution is hydrogen, straight or branched $(C_1-C_6)$alkyl, bromine, chlorine, fluorine, iodine, $(C_1-C_6)$alkoxy, difluoromethyl, trifluoromethyl]— 1,2,3,4-tetrahydro-(5 or 6)-naphthyl —[wherein the substitution is hydrogen, straight or branched $(C_1-C_6)$alkyl, bromine, chlorine, fluorine, iodine, $(C_1-C_6)$alkoxy, difluoromethyl, trifluoromethyl]— indanyl; or

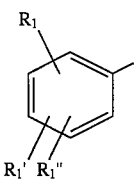

wherein $R_1'$, $R_1'$, and $R_1''$ are independently hydrogen, straight or branched $(C_1-C_6)$alkyl, bromine, chlorine, fluorine, iodine, $(C_1-C_6)$alkoxy, difluoromethyl, trifluoromethyl, trifluoromethoxy, difluoromethoxy, nitro, hydroxy, $(C_1-C_6)$hydroxyalkyl, —NR₅R₆ wherein $R_5$ and $R_6$ are independently hydrogen, straight or branched $(C_1-C_6)$alkyl, substituted phenyl, or substituted phenyl$(C_1-C_6)$alkyl, —SR₇ wherein $R_7$ is hydrogen or straight or branched $(C_1-C_6)$alkyl; carboxy, or $(C_1-C_6)$alkoxycarbonyl;

$R_2$ and $R_3$ are hydrogen or $(C_1-C_4)$alkyl;

m and n are integers from 0–1;

l is an integer from 0–3;

V is oxygen, NH or CH₂ and are ortho to each other;

W and U are independently hydrogen, hydroxy, —CO₂R₈ or —OCH₂CO₂R₈ wherein $R_8$ is hydrogen or straight or branched $(C_1-C_{10})$alkyl, —CONR₉R₁₀ or —OCH₂CONR₉R₁₀; wherein $R_9$ and $R_{10}$ are hydrogen, straight or branched $(C_1-C_{10})$alkyl, substituted benzyl, substituted phenyl, a heterocycle —(selected from the group consisting of pyridylmethyl, thienyl, furfuryl, furyl, pyrazolyl, imidazolyl, isothiazolyl, isoxazolyl, tetrazolyl, thiazolyl, 1,2,4-triazinyl and 1,2,4-triazolyl)— a saccharide residue or a peptide, cyano, cyano$(C_1-C_6)$alkyl chlorine, bromine, halo$(C_1-C_6)$alkyl, hydroxy$(C_1-C_6)$alkyl, hydroxymethylcarbonyl, SH, SO₃H, S(O)CH₃, SO₂CH₃, —CH₂SO₃H, —CH₂SR₁₁, —CH₂S(O)R₁₁ wherein $R_{11}$ is $(C_1-C_4)$alkyl, tetrazol-5-yl, or U and W taken together are carbonyl;

X is a divalent radical:

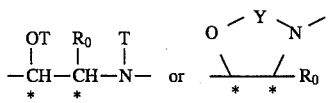

wherein $R_0$ is hydrogen or $(C_1-C_3)$alkyl;

T is hydrogen, $(C_1-C_4)$alkyl or $(C_1-C_4)$acyl;

Y is carbonyl or thiocarbonyl;

and the pharmaceutically acceptable salts and esters, the enantiomers, the racemic mixtures and diastereomeric mixtures thereof.

The compounds of the above formula I have centers of asymmetry at the carbon atoms marked with an asterisk (*). The compounds may, therefore, exist in at least two and often four stereoisomeric forms. The present invention encompasses all stereoisomers of the compounds whether free from other stereoisomers or admixed with other stereoisomers in any proportion and thus includes, for instance, racemic mixtures of enantiomers as well as the diastereomeric mixture of isomers. Preferably both asymmetric carbon atoms have the R absolute stereochemical configuration. The absolute configuration of any compound may be determined by conventional X-ray crystallography.

The preferred compounds of the present invention are disodium (R,R)-5-(3-((2-(3-chlorophenyl)2-hydroxyethyl)amino)butyl)-1,3-benzodioxole-2,2-dicarboxylate, (5-(2-((2-(3-chlorophenyl)-2-hydroxyethyl)-amino)propyl)-2,2-di(hydroxymethylcarbonyl)-1,3-benzodioxole disodium salt, [6-(2-(5-(3-chlorophenyl)-2-hydroxyethyl)amino)propyl)-1,4-benzodioxan-2-yl]-methanesulfonate, diethyl 5-[[2-(3-chlorophenyl)-2-hydroxyethyl)amino)methylbenz-imidazoline-2,2-dicarboxylate dihydrochloride, and disodium 5-(2-(3-chlorophenyl)-2-hydroxyethyl)aminomethyl-1,3-benzodioxole-2,2-dicarboxylate and the optically active derivatives thereof.

Also according to the present invention, there is provided a method of treating diabetes and/or hyperglycemia and/or obesity and/or inflammatory bowel disease, irritable bowel syndrome, non-specific diarrhea and dumping syndrome and/or depression and/or hyperlipidemia, hypertension, hypertriglyceridemia, hypercholesterolemia, atherosclerosis and conditions of low HDL in humans or other mammals which comprises administering to a human or other mammal an anti-obesity effective amount, or an anti-hyperglycemia effective amount or an anti-inflammatory bowel disease, anti-irritable bowel syndrome, anti-non-specific diarrhea and dumping syndrome effective amount, or antidepressant effective amount, or anti-hypertriglyceridemia effective amount, or anti-hypercholesterolemia effective amount, or anti-atherosclerosis effective amount, or reversal-of-a-condition-of-low-HDL effective amount of a compound of the present invention.

Further, according to the present invention there are provided pharmaceutical compositions of matter comprising an effective amount of the compound of the present invention in combination with a pharmaceutically acceptable carrier; as well as a method for increasing the content of lean meat in edible mammals, which comprises administering to edible mammals an effective amount of the compound. Also, the present invention provides processes for producing the compounds, salts and esters of the invention thereof.

DETAILED DESCRIPTION OF THE INVENTION

The disease diabetes mellitus is characterized by metabolic defects in production and utilization of glucose which result in the failure to maintain appropriate blood sugar levels. The result of these defects is elevated blood glucose or hyperglycemia. Reseach on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated levels of insulin and appears to be the result of an inability of tissues to respond appropriately to insulin. Most of the Type II diabetics are also obese.

SELECTIVITY

Current methods for the treatment of Type II diabetes and obesity employ beta adrenergic agents (Bloom, et el., U.S. Pat. No. 5,061,727), and particularly those that are selective for the beta$_3$-receptor. beta-Adrenergic receptors can be divided into beta1, beta$_2$, and beta$_3$-subtypes. Activation of beta$_1$-receptors invokes increases in heart rate while activation of beta$_2$-receptors stimulates glycogen breakdown in muscle and thereby prevents glycogen synthesis. Activation of beta$_3$-receptors stimulates lipolysis (the breakdown of adipose tissue triglycerides to glycerol and free fatty acids), and thereby promotes the loss of fat mass. Compounds that stimulate beta$_3$-receptors will have anti-obesity activity. In addition, they have hypoglycemic or antidiabetic activity, but the mechanism of this effect is unknown. A compound that selectively stimulates beta$_3$-receptors, i.e. has little or no beta$_1$ or beta$_2$-activity, will have the desired anti-diabetic and/or anti-obesity activity, but without the undesirable effects of increased heart rate (beta$_1$-effect) or muscle tremor (beta$_2$-effect).

Selectivity of a compound is determined using the following procedures.

Binding assays for $\beta_1$-effect are carried out by the use of membranes from rat heart, and $\beta_2$-effect by the use of membranes from rat lung by the method described in Neve, et at., J. Pharmacol. Exp. Ther., 1985, 235, 657–664 with the following exceptions:

1. the incubation volume is 0.5 ml,
2. the incubation time is 1 hour,
3. the radioligand is [$^{125}$I]iodocyanopindolol,
4. (−)-isoproterenol (50 μM) is used to define specific binding, and
5. the filters are washed at 4° C.

The $\beta_3$-effect of the compounds is determined by their ability to stimulate adipocyte lipolysis. Rat epididymal fat pads are excised and placed in 0.9% saline. Four grams of tissue is transferred to a flask with 20 ml of aerated Krebs-Henseleit bicarbonate (KHB) buffer containing 3% fatty acid-free bovine serum albumin to which 75 mg of crude bacterial collagenase (Worthington) has been added. The tissue is incubated for about 45 minutes at 37° C. with gentle shaking. The cells are then washed three times with two volumes of KHB buffer, filtered through two layers of gauze, and brought to a final volume of 80 ml with KHB buffer. One ml aliquots of the cell suspension is added to plastic test tubes containing the appropriate additions of vehicle or compound. The cells are gassed for 1 minute with 95%O$_2$-5%CO$_2$, capped, and incubated at 37° C. with continuous shaking for a total of 30 minutes. The reaction is stopped by adding 0.1 ml of 30% perchloric acid and 0.1 ml of chloroform. After centrifugation, 0.5 ml of supernatant is transferred to another test tube and neutralized with 0.04 ml of 3M K$_2$CO$_3$-0.5M triethanolamine. The amount of glycerol generated from the hydrolysis of endogenous triglycerides is determined in a coupled-enzyme spectrophotometric assay. One-tenth milliliter of the neutralized extract is added to a test tube that contains 0.91 ml of assay mixture comprised of the following: 0.84M glycine, 0.42M hydrazine sulfate, 4.2 mM EDTA, 0.9 mM beta-NAD, 9.9 mMMgCl$_2$, 1mMATP, 17 U of glycerophosphate dehydrogenase, and 4.3 U of glycerokinase. The test tubes are incubated for 40 minutes at 37° C. with constant shaking. The amount of NADH generated, which is proportional to the amount of glycerol, is determined by the increase in absorbance at 340 nm. This value is corrected for the amount of NADH generated in the absence of glycerol by incubating another aliquot of the neutralized extract with the same assay mixture but without glycerokinase. The molar ED$_{50}$ value is the molar concentration of compound that gives 50% of the maximum rate of lipolysis of that compound.

TABLE 1

| | Beta$_3$-Selectivity Comparison | | |
|---|---|---|---|
| Example # | Lipolysis (beta$_3$) (EC$_{50}$nM) | Heart Binding (IC$_{50}$nM) | Lung Binding (IC$_{50}$ nM) |
| 3 | 17 | 19,000 | 20,000 |

Selective agonists of the beta$_3$-adrenoceptor have demonstrated potential utility in the treatment of disorders of the gastrointestinal tract, such as: inflammatory bowel disease, irritable bowel syndrome, non-specific diarrhea and dumping syndrome (Holloway, B. R., et. al., EP516349-A2 and EP516350-A2, Dec. 2, 1992).

These compounds may also be useful in the treatment of hyperlipidemia, hypertension, hypertriglyceridemia, hypercholesterolemia, atherosclerosis, and conditions of low HDL (high density lipoprotein) (Holloway, B. R., see above).

Additionally, these compounds may be useful in the treatment of central nervous system disorders such as depression, in which an agonist of the beta$_3$-adrenoceptor is involved (Simiand, J., et al., European Journal of Phrmacology, 219(1992) pp. 193–201).

The compounds of the present invention may generally be prepared according to Schemes 1–12.

SCHEME 1

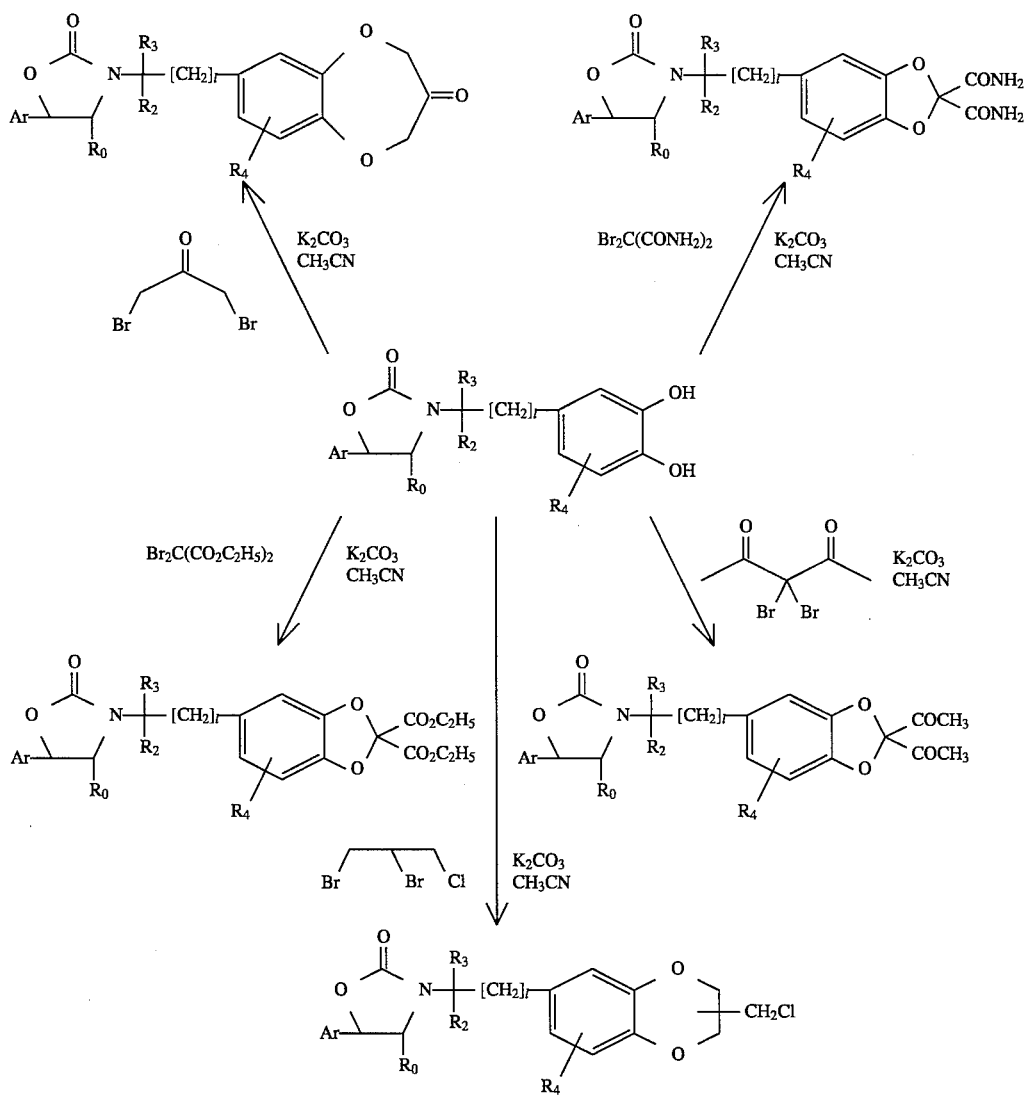

According to Scheme 1, a compound of formula:

7

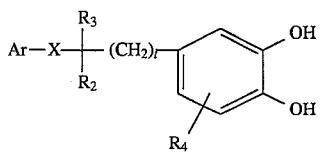

wherein Ar, X, $R_0$, $R_2$, $R_3$, $R_4$ and l are as defined hereinabove; is reacted with a compound of the formula:

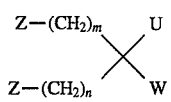

wherein Z is chlorine, bromine or iodine; m and n are as defined hereinabove; U and W are as defined hereinabove with the proviso that when U and/or W are —$CONR_9R_{10}$, $R_9$ and $R_{10}$ are hydrogen or ($C_1$–$C_{10}$) alkyl, and U and W are not —SH, —$SO_3H$, —S (O) $CH_3$, —$SO_2CH_3$, alkyl($C_1$–$C_6$)$SO_3H$, alkyl($C_1$–$C_6$)$SR_{11}$, or alkyl($C_1$–$C_6$)S(O)$R_{11}$; in the presence of a base such as potassium carbonate, sodium carbonate or cesium carbonate, in a solvent such as acetone or acetonitrile, at 10° C. to 80° C. for from 1 to 72 hours to give a compound of the formula:

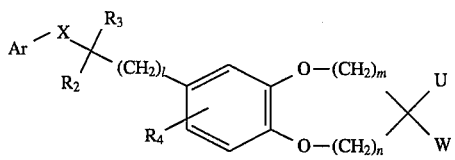

wherein Ar, X, $R_0$, $R_2$, $R_3$, $R_4$, U, W, l, m and n are as defined hereinabove for formulae II and III.

According to Scheme 1, a compound of the formula:

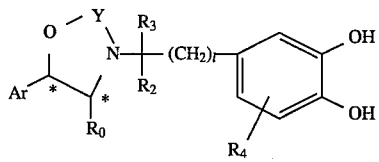

wherein Ar, Y, $R_0$, $R_2$, $R_3$, $R_4$ and l are as defined hereinabove; is reacted with a compound of formula III wherein Z is as defined hereinabove, and U and W are both $CH_3C(=O)$— and m and n are zero; in the presence of a base such as potassium carbonate or cesium carbonate, in a solvent such as acetonitrile at 10° to 40° C. for from 1 to 72

8 hours to give a compound of formula:

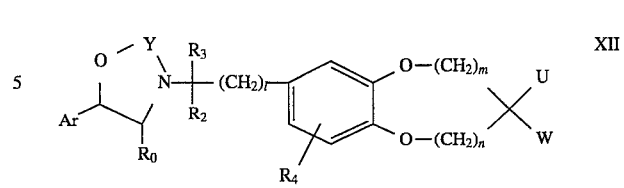

wherein At, Y, $R_0$, $R_2$, $R_3$, $R_4$ and l are as defined hereinabove, U and W are both acetyl, and m and n are zero.

SCHEME 2

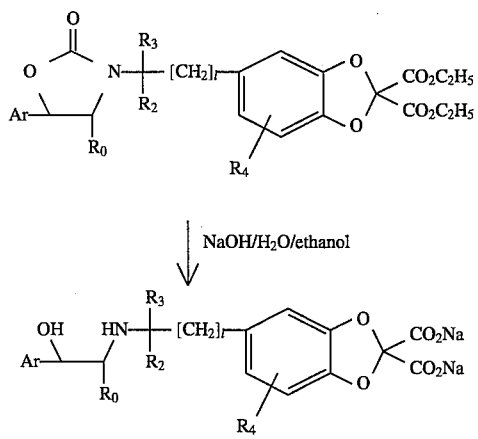

According to Scheme 2, a compound of formula IV wherein Ar, X, $R_2$, $R_3$, $R_4$, l, m, and n are as defined hereinabove; is reacted with a base such as sodium hydroxide or potassium hydroxide at 60° C. to 100° C. for from 1 to 24 hours to give a compound of formula IV wherein Ar, $R_2$, $R_3$, $R_4$, l, m, and n are as defined hereinabove, X is

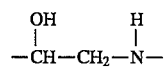

and U and W are hydrogen, hydroxy, tetrazol-5-yl, cyano cyano ($C_1$–$C_4$)alkyl —$CORM_2^-M^+$, or —OCH $CO_2^-M^+$, wherein $M^+$ is sodium or potassium,

SCHEME 3

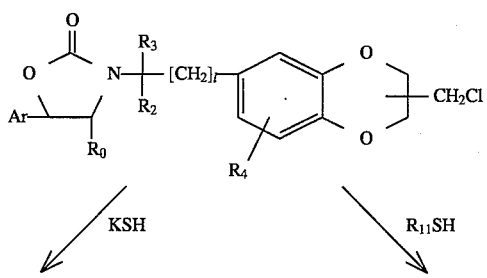

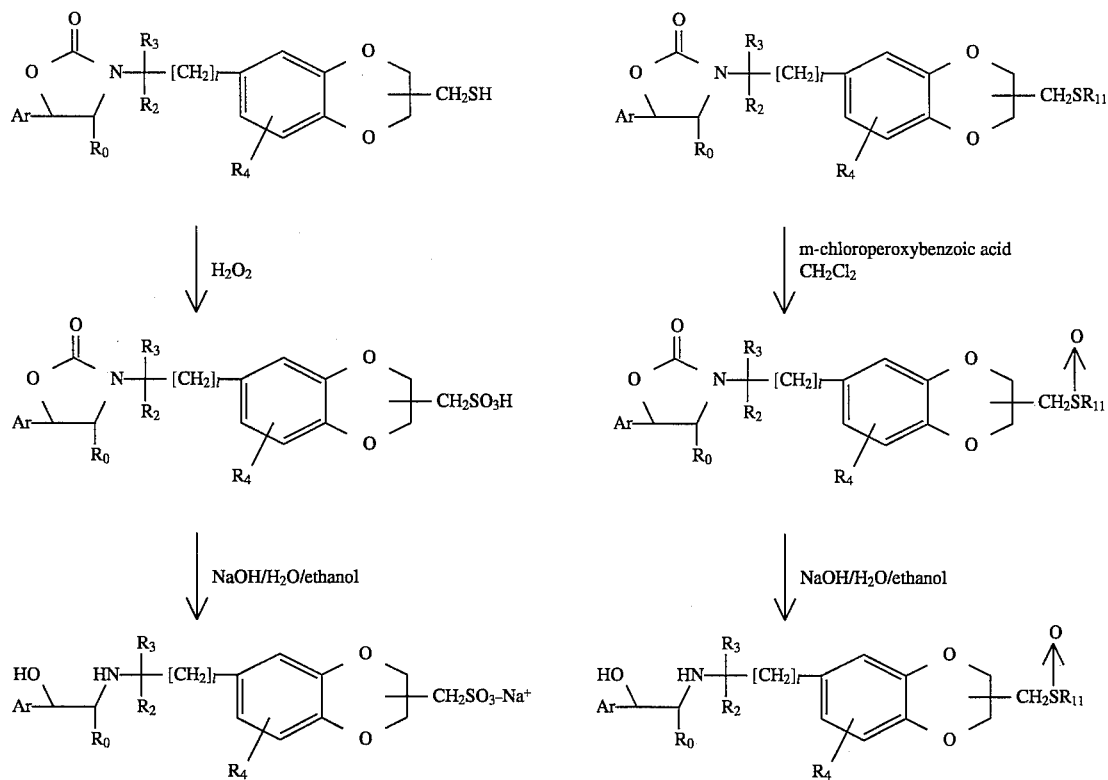

According to Scheme 3, a compound of formula IV wherein Ar, X, $R_2$, $R_3$, $R_4$, Z, l, m, and n are as defined in formulae II and III, and where U and W are bromine, chlorine or iodine and at least one is hydrogen; or halo($C_1$–$C_6$)alkyl (the halo is bromine, chlorine or iodine) is reacted with a nucleophile such as potassium hydroxide, potassium hydrosulfide or $NaSR_{11}$ in a solvent such as ethyl alcohol, dimethylsulfoxide or acetonitrile at 20° C. to 80° C., for 1 to 12 hours to give a compound of formula IV wherein Ar, x, $R_2$, $R_3$, $R_4$, Z, l, m, and n are as defined hereinabove, and U and W are hydroxy, hydroxy($C_1$–$C_6$)alkyl, —SH, —SH($C_1$–$C_6$)alkyl, —$SR_{11}$ and —$SR_{11}$ ($C_1$–$C_6$)alkyl and $R_{11}$ is as defined hereinabove.

A compound of formula IV wherein Ar, X, $R_2$, $R_3$, $R_4$, l, m, and n are as defined hereinabove, U and W are SH, SH($C_1$–$C_6$)alkyl, $SR_{11}$, and $SR_{11}$ ($C_1$–$C_6$)alkyl, and $R_{11}$ is as defined hereinabove; is oxidized with an agent such as hydrogen peroxide or m-chloroperoxybenzoic acid in a solvent such as ethyl alcohol, acetic acid or methylene chloride at 0° to 25° C. for from 15 minutes to 10 hours to give a compound of formula IV wherein Ar, X, $R_2$, $R_3$, $R_4$, l, m, and n are as defined hereinabove, U and W are —$SO_3H$, ($C_1$–$C_6$)alkyl-$SO_3H$, —$SOR_{11}$, ($C_1$–$C_6$)alkyl-$S(O)R_{11}$, —$SO_2R_{11}$, and ($C_1$–$C_6$)alkyl-$SO_2R_{11}$ and $R_{11}$ is as defined hereinabove.

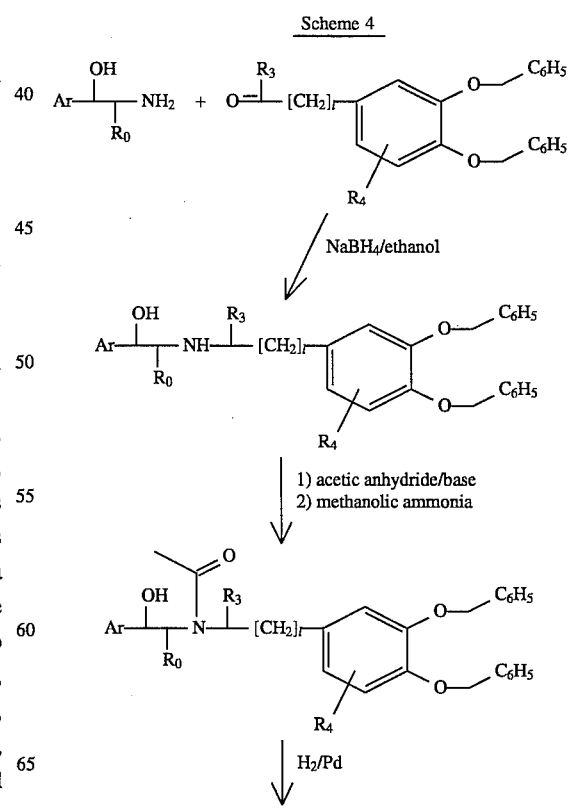

Scheme 4

-continued
Scheme 4

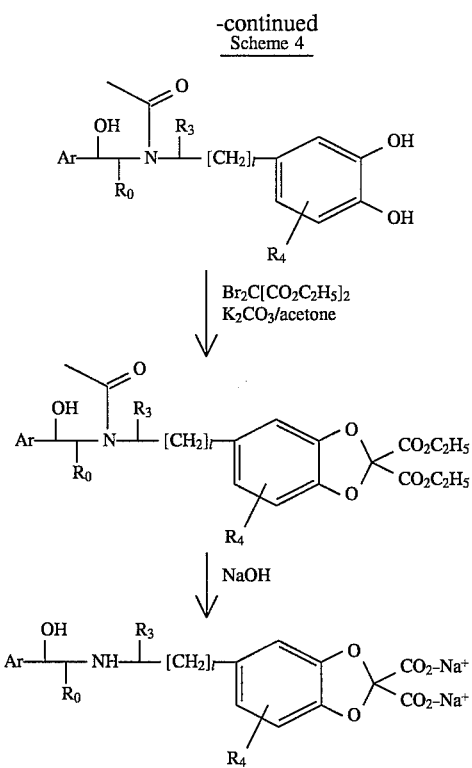

According to Scheme 4, a compound of formula:

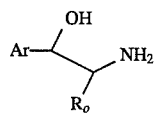

wherein Ar and $R_0$ are as defined hereinabove; is reacted with a compound of formula:

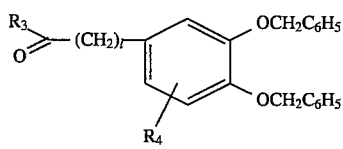

wherein $R_3$, $R_4$ and l are as defined hereinabove; in a solvent such as ethyl alcohol or tetrahydrofuran and adding a reducing agent such as sodium borohydride or sodium triacetoxyborohydride at 0° to 40° C. for from 30 minutes to 4 hours, to give a compound of the formula:

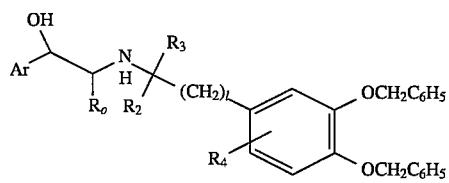

wherein Ar, $R_0$, $R_2$, $R_3$, $R_4$ and l are as defined hereinabove.

A compound of formula VII wherein Ar, $R_0$, $R_2$, $R_3$, $R_4$ and l are as defined hereinabove; is acetylated with acetic anhydride in pyridine, followed by treatment with methanolic ammonia at 0° to 25° C. for from 1 to 18 hours to give a compound of formula:

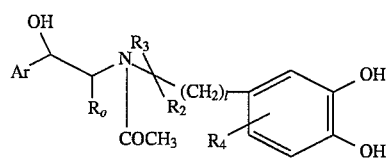

wherein Ar, $R_0$, $R_2$, $R_3$, $R_4$ and l are as defined hereinabove.

A compound of formula VIII wherein Ar, $R_0$, $R_2$, $R_3$, and l are as defined hereinabove; is reacted with a compound of formula III wherein Z, U, W, m and n are as defined hereinabove; in the presence of potassium carbonate at 10° to 80° C. in acetone or acetonitrile for from 1 hour to 72 hours to give a compound of formula:

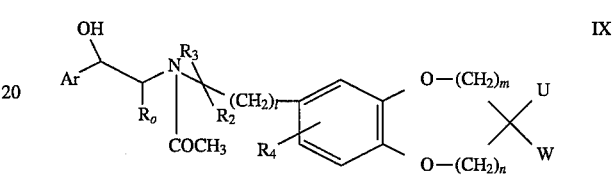

wherein At, $R_0$, $R_2$, $R_3$, U, W, l, m, and n are as defined hereinabove.

A compound of formula IX wherein Ar, $R_0$, $R_2$, $R_3$, U, W, l, m, and n are as defined hereinabove; is combined with sodium hydroxide in ethyl alcohol and water at 60° to 90° C. for from 2 to 36 hours to give a compound of formula IX wherein Ar, $R_0$, $R_2$, $R_3$, $R_4$, U, W, l, m, and n are as defined hereinabove.

SCHEME 5

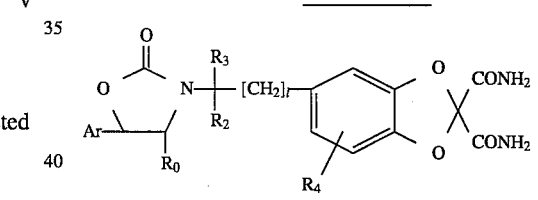

↓ POCl₃

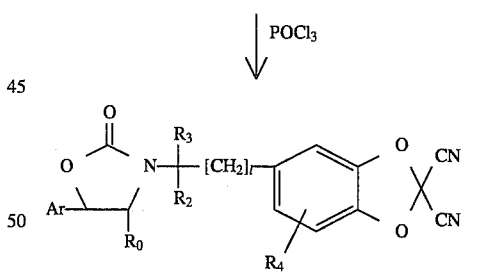

↓ NaN₃/(n-C₄H₁₀)₃SnCl/toluene

↓ NaOH

-continued
SCHEME 5

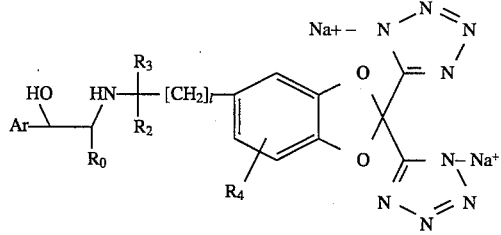

According to Scheme 5, a compound of formula IV wherein Ar, X, $R_2$, $R_3$, $R_4$, l, m, and n are as defined hereinabove, and U and W are —$CONH_2$ or hydrogen, with the proviso that U and W are not both hydrogen; is reacted with an agent for removing the elements of water, such as phosphorus oxychloride or dicyclohexylcarbodiimide in a solvent such as chloroform or tetrahydrofuran at 25° to 100° C. for from one hour to 36 hours to give a compound of formula IV wherein Ar, X, $R_2$, $R_3$, $R_4$, l, m, and n are as defined hereinabove, and U and W are cyano or hydrogen, with the proviso that U and W are not both hydrogen.

A compound of formula IV, wherein Ar, X, $R_0$, $R_2$, $R_3$, $R_4$, l, m, and n are as defined hereinabove and U and W are cyano or hydrogen with the proviso that U and W are not both hydrogen; is reacted with tri(n-butyl)tin chloride and sodium azide in a solvent such as tetrahydrofuran or toluene at 0° to 40° C. for from 15 minutes to 6 hours to give a compound of formula IV wherein Ar, X, $R_0$, $R_2$, $R_3$, $R_4$, l, m, and n are as defined hereinabove and U and W are 5-tetrazolyl or hydrogen with the proviso that U and W are not both hydrogen.

SCHEME 6

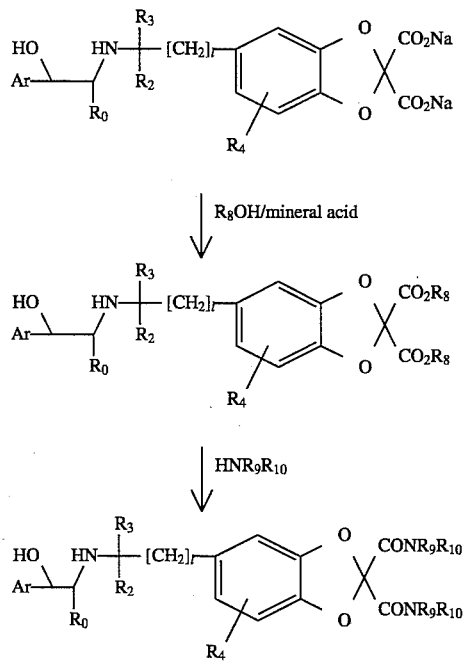

According to Scheme 6, a compound of formula:

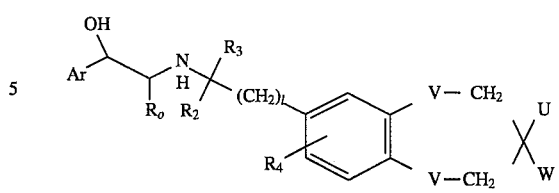

wherein Ar, $R_0$, $R_2$, $R_3$, $R_4$, V, l, m, and n are as defined hereinabove, and U and W are $CO_2R_8$ or hydrogen and $R_8$ is as defined hereinabove, with the proviso that U and W are not both hydrogen; is reacted with an amine $HNR_9R_{10}$, wherein $R_9$ and $R_{10}$ are as defined hereinabove, at 25 to 100° C. in a solvent such as ethyl alcohol, tetrahydrofuran, or dioxane for from 1 to 36 hours to give a compound of formula X wherein Ar, $R_0$, $R_2$, $R_3$, $R_4$, V, l, m, and n are as defined hereinabove and U and W are $CONR_9R_{10}$ and $R_9$ and $R_{10}$ are as defined hereinabove.

A compound of formula X wherein Ar, $R_0$, $R_2$, $R_3$, $R_4$, V, l, m, and n are as defined hereinabove and U and W are —$CO_2^-M^+$, and $M^+$ is a metal such as sodium or potassium; is reacted with an alcohol $R_8OH$, wherein $R_8$ is as defined hereinabove, at 25° to 100° C. in the presence of an acid such as hydrochloric acid, sulfuric acid, p-toluenesulfonic acid for from 1 to 24 hours to give a compound of formula X wherein Ar, $R_0$, $R_2$, $R_3$, $R_4$, V, l, m, and n are as defined hereinabove and U and W are —$CO_2R_8$ and $R_8$ is as defined hereinabove.

SCHEME 7

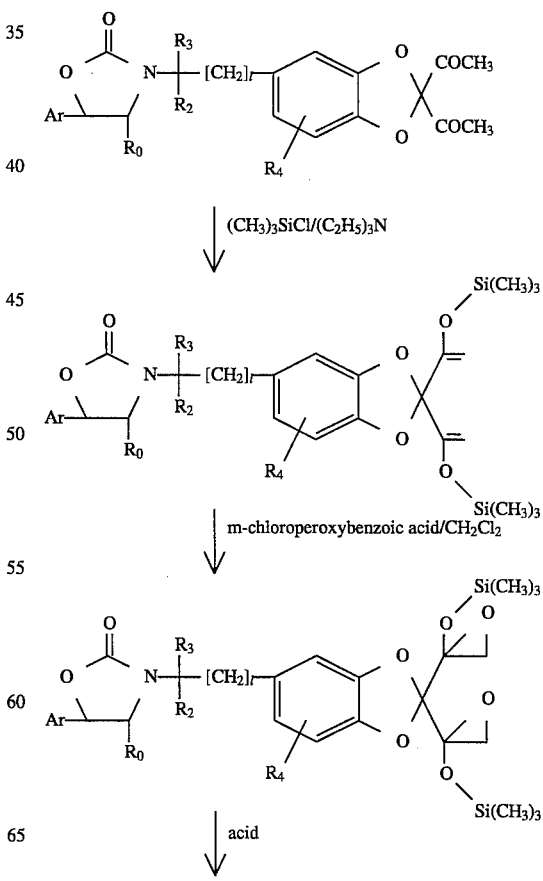

-continued
SCHEME 7

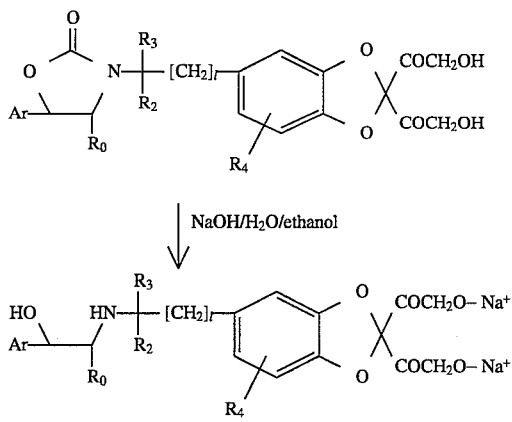

According to Scheme 7, a compound of formula XI wherein Ar, Y, $R_0$, $R_2$, $R_3$, $R_4$, and l are as defined hereinabove, U and W are both acetyl, and m and n are zero; is reacted with a silylating agent, such as trimethylsilyl chloride in the presence of a base such as diisopropylethyl amine, in a solvent such as tetrahydrofuran, at 0° to 40° C. for from 30 minutes to 4 hours to give a compound of formula XII wherein Ar, Y, $R_0$, $R_2$, $R_3$, $R_4$, l, m and n are as defined hereinabove, and U and W are both

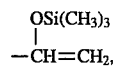

and then a compound of formula XII wherein Ar, Y, $R_0$, $R_2$, $R_3$, $R_4$, U, W, l, m and n are as defined hereinabove, and U and W are both

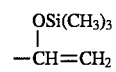

is reacted with an oxidizing agent such as m-chloroperoxybenzoic acid in a solvent such as methylene chloride at −10° to 25° C. for from 30 minutes to 4 hours to give a compound of formula XII wherein Ar, Y, $R_0$, $R_2$, $R_3$, $R_4$, l, m and n are as defined hereinabove and U and W are both

and then a compound of formula XII wherein Ar, Y, $R_0$, $R_2$, $R_3$, $R_4$, l, m and n are as defined hereinabove and U and W are both

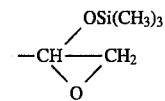

is reacted with an acid such as sulfuric acid or p-toluenesulfonic acid in a solvent such as tetrahydrofuran to give a compound of formula XII wherein Ar, y, $R_1$, $R_2$, $R_3$, $R_4$, l, m and n are as defined hereinabove and U and W are —C(=O)CH$_2$OH.

A compound of formula XII wherein Ar, Y, $R_0$, $R_2$, $R_3$, $R_4$, l, m and n are as defined hereinabove and U and W are —C(=O)CH$_{20}$H; is combined with sodium hydroxide in ethyl alcohol-water and heated at 50 to 80° C. for from 1 to 24 hours, and the product is isolated by ion exchange chromatography to give a compound of formula I wherein Ar, X, $R_2$, $R_3$, $R_4$, l, m and n are as defined hereinabove, V is oxygen, m and n are both zero and U and W are both —C(=O)CH$_2$O$^-$Na$^+$.

SCHEME 8

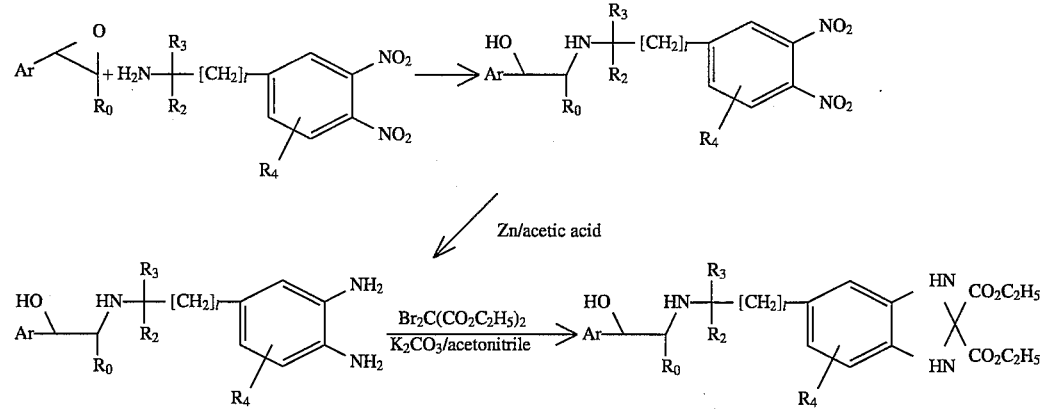

According to Scheme 8, a compound of formula:

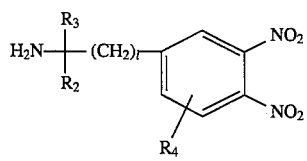 XIII wherein $R_2$, $R_3$ $R_4$ and l are as defined hereinabove; is reacted with a compound of formula:

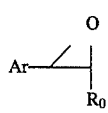

wherein Ar and $R_0$ are as defined hereinabove; in a solvent such as ethyl alcohol at 10° to 100° C. for from 1 to 32 hours to give a compound of formula:

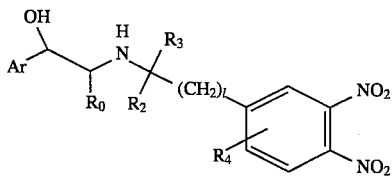 XIV wherein Ar, $R^o$, $R_2$, $R_3$, $R_4$ and l are as defined hereinabove.

A compound of formula XIV wherein Ar, $R_0$, $R_2$, $R_3$, $R_4$ and l are as defined hereinabove; is reacted with a reducing agent such as zinc in acetic acid, for from 30 minutes to 2 hours at 0° to 50° C. to give a compound of formula:

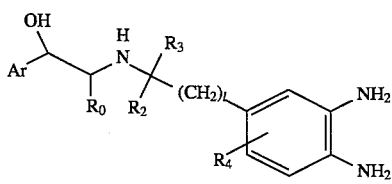 XV wherein Ar, $R^o$, $R_2$ $R_3$ $R_4$ and l are as defined hereinabove.

A compound of formula XV wherein Ar, $R_o$, $R_2$, $R_3$, $R_4$ and l are as defined hereinabove; is reacted with a compound of formula:

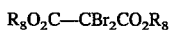

to give a compound of formula:

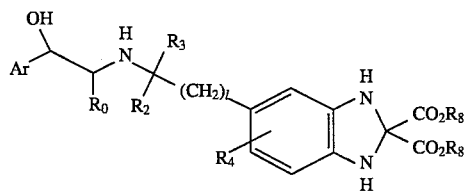 XVI wherein Ar, $R_0$, $R_2$, $R_3$, $R_4$ $R_8$ and l are as defined hereinabove.

SCHEME 9

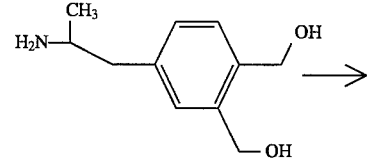

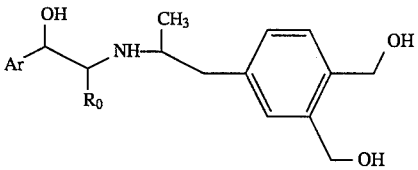

1) acetic anhydride/pyridine
2) methanolic ammonia

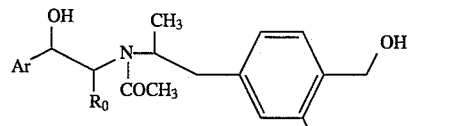

CH$_3$SO$_2$Cl/pyridine

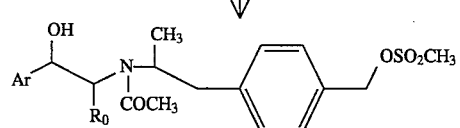

diethyl malonate/base

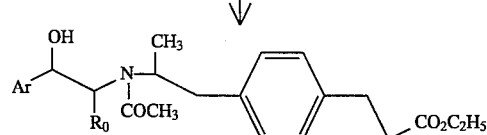

NaOH

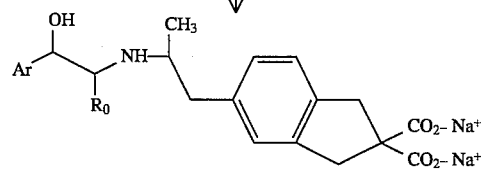

According to Scheme 9, a compound of formula:

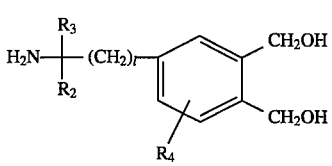

wherein $R_2$, $R_3$, $R_4$ and l are as defined hereinabove; is reacted with a compound of the formula:

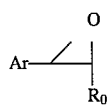

wherein Ar and $R_0$ are as defined hereinabove; to give a compound of formula:

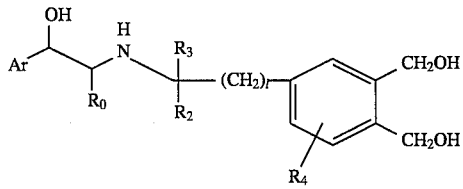

wherein Ar, $R_0$, $R_2$, $R_3$, $R_4$ and l are as defined hereinabove.

A compound of formula XVII wherein Ar, $R_0$, $R_2$, $R_3$, $R_4$ and l are as defined hereinabove; is reacted with acetic anhydride in pyridine, then allowed to stand in a solution of methanolic ammonia at 0° to 25° C. for from one to 18 hours to give a compound of formula:

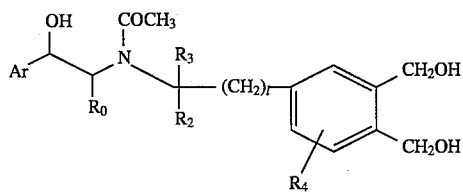

wherein Ar, $R_0$, $R_2$, $R_3$, $R_4$ and l are as defined hereinabove.

A compound of formula XVIII wherein Ar, $R_0$, $R_2$, $R_3$, $R_4$ and l are as defined hereinabove; is reacted with a sulfonylating reagent such as methanesulfonyl chloride or p-toluenesulfonyl chloride to give a compound of formula:

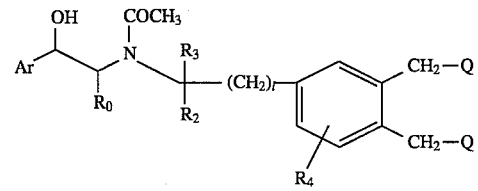

wherein Ar, $R_0$, $R_2$, $R_3$, $R_4$ and l are as defined hereinabove, and Q is

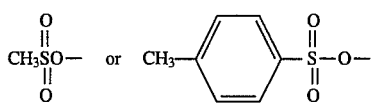

A compound of formula XIX wherein Ar, $R_0$, $R_2$, $R_3$, $R_4$, Q and l are as defined hereinabove, is reacted with a compound of formula:

$$R_8O_2CCH_2CO_2R_8$$

in the presence of a base, such as sodium methoxide or sodium hydride in a solvent such as tetrahydrofuran at 0° to 60° C. for from 1 to 48 hours, to give a compound of formula:

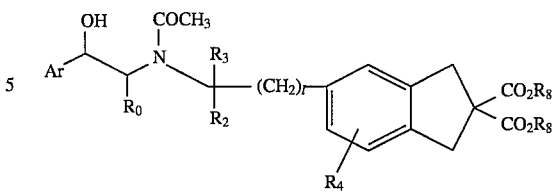

wherein $R_2$ is hydrogen and Ar, $R_0$, $R_3$, $R_4$ and $R_8$ are as defined hereinabove.

A compound of formula XX wherein $R_2$ is hydrogen and Ar, $R_0$, $R_3$, $R_4$ and $R_8$ are as defined hereinabove; is reacted with a base such as sodium hydroxide, in a solvent such as ethyl alcohol, at 25° to 80° C. for from one to 8 hours to give a compound of formula:

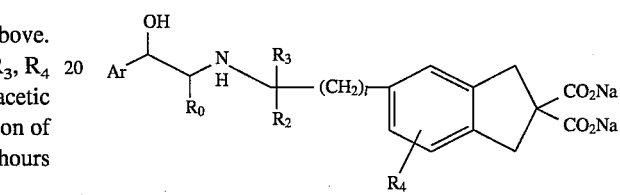

wherein Ar, $R_0$, $R_2$, $R_3$, $R_4$ and l are as defined hereinabove.

SCHEME 10

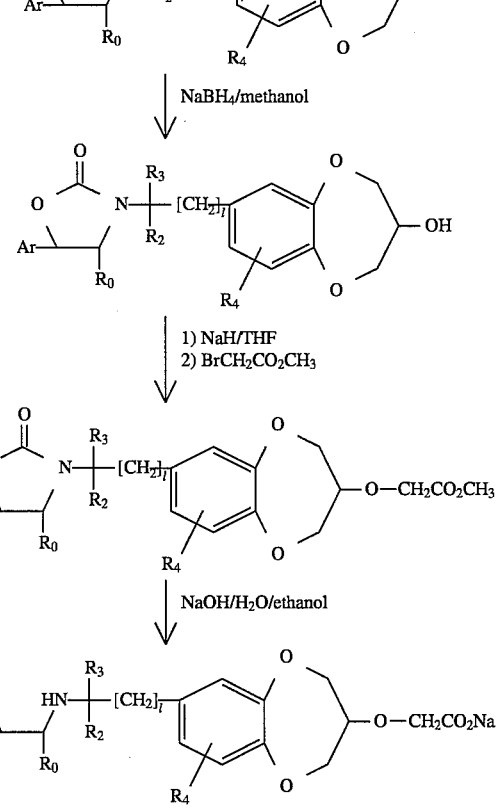

According to Scheme 10, a compound of formula IV, wherein Ar, X, $R_2$, $R_3$, $R_4$, l, m, and n are as defined hereinabove and U and W taken together are carbonyl, is reduced with a hydride reducing agent such as sodium borohydride in a solvent such as water, tetrahydrofuran or ethyl alcohol, at 0°–40° C. for from 1 to 4 hours to give a compound of formula IV wherein U is hydroxy and W is hydrogen; and this compound is reacted with a base such as sodium hydride in a solvent such as tetrahydrofuran at 0°–40° C. for from 40 minutes to 1 hour, followed by an alkylating agent such a methyl bromoacetate at 0°–40° C. and allowing this to stand for from 1 to 8 hours to give a compound of formula IV as defined hereinabove wherein U is —OCH$_2$CO$_2$CH$_3$, and W is hydrogen; then this is reacted with sodium hydroxide in a solvent such as water and ethanol, at 25° C. to 100° C. for from 1 to 24 hours to give a compound of formula XXII:

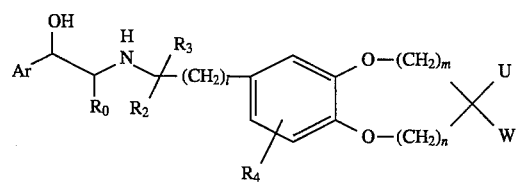

Scheme 11

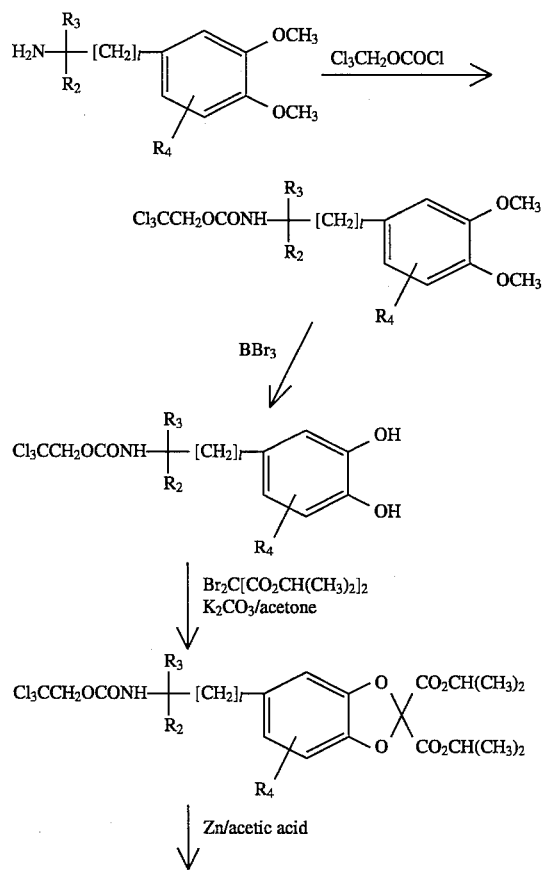

-continued
Scheme 11

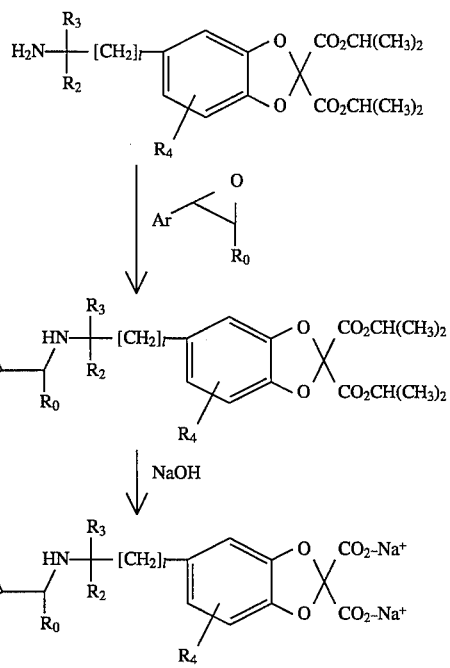

According to Scheme 11, a compound of formula:

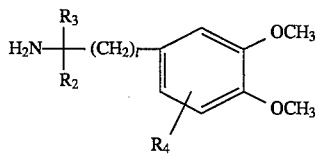

wherein R$_2$, R$_3$, and R$_4$ are as defined hereinabove, is reacted with a chloroformate such as Cl$_3$CH$_2$OCOCl in the presence of a base such as sodium hydroxide in a solvent such as water at 0°–40° C. for from 30 minutes to 4 hours to give a urethane of formula;

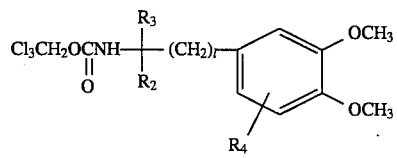

wherein R$_2$, R$_3$, R$_4$ and l are as defined hereinabove, and this compound is reacted with a a demethylating agent such as BBr$_3$ in a solvent such as methylene chloride at 0°–25° C. for from 30 minutes to 4 hours to give a catechol of formula:

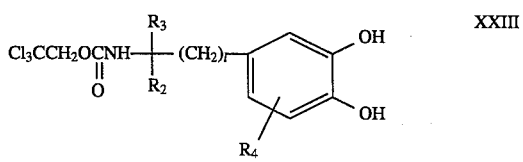

wherein $R_2$, $R_3$, $R_4$ and l are as defined hereinabove.

A compound of formula XXIII is reacted with a dihalodiester such as diisopropyl dibromomalonate in the presence of an acid scavenger such as potassium carbonate in a solvent such as acetone at 20°–60° C. for from 1–18 hours to give a compound of formula:

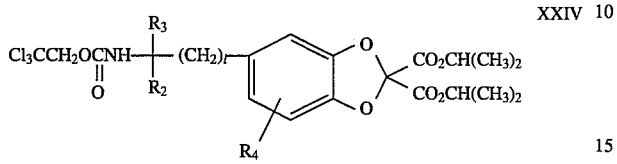   XXIV wherein $R_2$, $R_3$, $R_4$ and l are as defined hereinabove.

A compound of formula XXIV is reacted with a metallic reducing agent such as zinc in an acid solution such as acetic acid at 10°–80° C. to give an amine of formula:

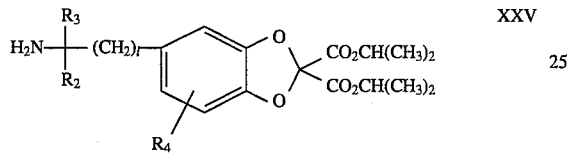   XXV wherein $R_2$, $R_3$, $R_4$ and l are as defined hereinabove.

A compound of formula XXV is reacted with an epoxide of formula:

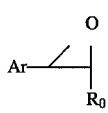

wherein Ar and $R_0$ are as defined hereinabove, to give a compound of formula I wherein AR, $R_2$, $R_3$, $R_4$ and l are as defined hereinabove, and X is

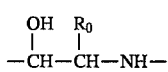

is oxygen, m and n are 0, U and V are both —$CO_2R_8$ and $R_8$ is as defined hereinabove.

Scheme 12

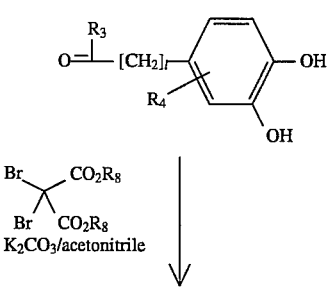

-continued
Scheme 12

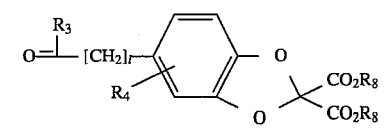

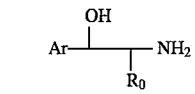
NaBH$_4$/ethanol

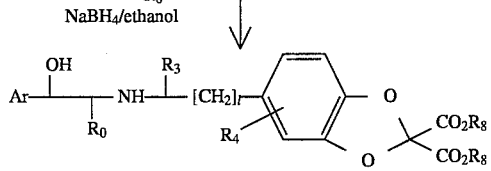

According to Scheme 12, a catechol of formula:

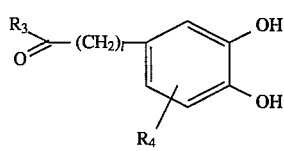

wherein $R_3$, $R_4$ and l are as defined hereinabove, is reacted with a dibromo diester of formula $Br_2C(CO_2R_8)_2$ and $R_8$ is as defined hereinabove, to give a compound of formula:

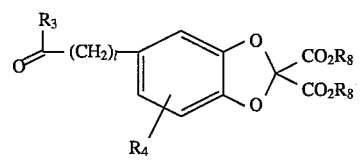   XXVI wherein $R_3$, $R_4$, $R_8$ and l are as defined hereinabove.

A compound of formula XXVI is reacted with an amine of formula V;

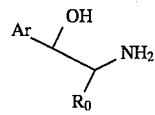

wherein Ar and $R_0$ are as defined hereinabove, to give a compound of formula I:

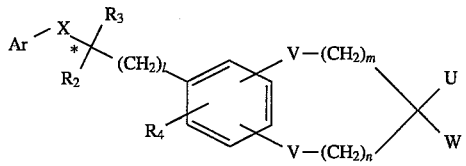

wherein Ar, $R_2$, $R_3$, $R_4$, $R_8$ and l are as defined hereinabove, and X is

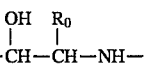

V is oxygen, m and n are 0, and U and V are both —$CO_2R_8$ and $R_8$ is as defined hereinabove.

The above mentioned patents and publications are incorporated herein by reference.

When the compounds are employed as anti-diabetic or antiobesity agents, they can be combined with one or more pharmaceutically acceptable carriers, for example, solvents, diluents and the like, and may be administered orally in such forms astablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose ann kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserve against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

Many variations of the present invention will suggest themselves to those who are skilled in the art in light of the above mention detailed description. All such obvious modifications are within the full intended scope of the appended claims.

The invention will be more fully described in conjunction with the following specific examples which are not to be construed as limiting the scope of the invention.

EXAMPLE 1

(R,S)-5-(3-Chlorophenyl-3-[(3,4-dimethoxyphenyl)-butan-2-yl]oxazolidinone and (R,R)-5-3-(3-chlorophenyl)-3-[(3,4-dimethoxyphenyl)-butan-2-yl]oxazolidinone A mixture of 41.4 g of 4-(3,4-dimethoxy-phenyl)-2-butanone and 41.9 ml of formamide is heated at 210° C. for 20 hours, cooled to ambient, 104 ml of 10N sodium hydroxide is added and the reaction mixture heated at reflux temperature for 24 hours. The reaction is cooled, added to 200 ml of water and extracted with diethyl ether. The diethyl ether solution is washed with 10% hydrochloric acid. The aqueous layer is made basic and extracted with diethyl ether. The organic layer is dried, filtered and evaporated in vacuo. The residue is purified by chromatography (silica gel: chloroform/hexane/ethyl acetate to 5% methyl alcohol/chrloroform) to give 5.72 g of racemic 2-amino-4-(3,4-dimethoxyphenyl)butane.

$^1$HNMR (CDCl$_3$): δ 6.77(m,3H,Ar); 3.88(s,3H,OCH$_3$); 3.86(s,3H,OCH$_3$); 2.93(m, 1H,CH); 2.61(m,2H,CH$_2$); 1.64(m,2H,CH$_2$); 1.43(br,2H,NH$_2$); 1.12(d,3H,Me,J=6.3 Hz).

A room temperature mixture, under argon, of 6.62 g of the above racemic mixture, 35 ml of dimethylsulfoxide and 4.57 g of trimethylsilylacetamide is stirred for 1 hour. A solution of 5.14 g of (R)-m-chlorostyrene oxide in 6 ml of dimethylsulfoxide is added and the reaction mixture is heated at 65°–70° C., under argon, for 48 hours. After cooling to room temperature, the reaction is added to 100 g of ice containing 8 ml of concentrated hydrochloric acid and the mixture is stirred for 15 minutes. The aqueous layer is extracted with diethyl ether, then made basic with 10N sodium hydroxide and extracted with diethyl ether. The organic extract is dried, filtered and evaporated in vacuo to give 6.64 g of 1-(m-chlorophenyl)-2-[4(3,4-dimethoxyphenyl)butan-2-yl]aminoethanol as a yellow oil. To this residue is added 40 ml of anhydrous tetrahydrofuran, 17.7 ml of triethylamine, and 6.4 g of carbonyldiimidazole. The reaction mixture is stirred at room temperature, under argon, for 20 hours, quenched with 200 ml of water and extracted with diethyl ether. The organic extracts are combined, washed with 2N hydrochloric acid and saturated sodium chloride, dried, filtered and evaporated in vacuo to give 2.54 g of a light yellow oil. The diastereomers are separated and purified by column chromatography (silica gel: chloroform/hexanes/ethyl acetate 3:6:1) to give 0.80 g of the (R,S) isomer (less polar) and 0.76 g of the (R,R) isomer (more polar).

(R;S) isomer $^1$HNMR (CDC$_{13}$) :6 7.34(m,3H,Ar); 7.26(m,1H,Ar); 6.82(d,1H,Ar,J=7.9 Hz); 6.74(m,2H,Ar); 5.30(t,1H,CH,J=

8.2 Hz); 4.08(m,1H,CH); 3.90(s,3H,OCH$_3$); 3.87(s,3H, OCH$_3$); 3.70(t,1H,CH,J=8.7 Hz); 3.29(t,1H,CH,J=8.2 Hz); 2.64(m,2H, CH$_2$); 181(m,2H,CH$_2$); 1.17(d, 3H,Me,J=6.8 Hz).

(R,R) isomer $^1$HNMR (CDCl$_3$): δ7.35(m,3H,Ar); 7.25(m, 1H,Ar); 6.76(d, 1H,Ar,J=8.3 Hz); 6.62(m,2H,Ar); 5.49(dd, 1H,CH, J=6.5, 8.8 Hz); 4.06(m,1H,CH); 3.90(t,1H, CH,J=8.8 Hz); 3.86(s,3H,OCH$_3$); 3.84(s,3H,OCH$_3$); 3.28(dd,1H,CH,J=6.5, 8.7 Hz); 2.50(m,2H,CH$_2$); 1.73(m,2H,CH$_2$); 1.23(d,3H,Me, J=6.8 Hz).

EXAMPLE 2

Disodium (R,S)-5-(3-(2-(3-chlorophenyl)-2-hydroxyethyl)amino)butyl)- 3-benzodioxole-2,2-dicarboxylate To a 0°–4° C. solution, under argon, of 0.80 g of the (R,S) isomer from Example 1 in 15 ml of methylene chloride is added, dropwise, 6.2 ml of 1M boron tribromide. The reaction temperature is maintained below 4° C. for 20 minutes, then allowed to warm to ambient temperature and stirred for an additional hour. The reaction mixture is cooled to 5° C. quenched with 10 ml of water and stirred at room temperature for one hour. The formed solids are redissolved using water and ethyl acetate and the layers are separated. The organic layer is washed with saturated sodium chloride, dried, filtered and evaporated in vacuo to give a yellow oil. The oil is dissolved in acetone and treated, under argon, with 0.57 g of powdered potassium carbonate and 0.72 g of diethyl dibromomalonate. The reaction mixture, is stirred, under argon, for 18 hours. The inorganic solids are collected and washed with acetone. The combined filtrates are evaporated in vacuo to give a light brown oil. The oil is purified by column chromatography (silica gel: 100 ml of methylene chloride; 100 ml of methylene chloride:hexanes:ethyl acetate 1:1:1). The 1:1:1 eluates are evaporated in vacuo to give a light yellow oil. Re-chromatography of the yellow oil (silica gel: toluene:acetone 20:1) gives 0.38 g of diethyl (R,S)-[5-(3-chlorophenyl)-2-oxo-3-oxazolidinyl]-1,3-dioxole-2,3-dicarboxylate.

$^1$HNMR (CDCl$_3$) : 67.33(m,3H,Ar); 7.12(m,2H,Ar); 6.86(d, 1H,Ar,J=8.0Hz); 6.81 (d,1H,Ar,J=1.2 Hz); 6.74(dd, 1H,Ar,J=8.0, 1.4 Hz); 5.33(t, 1H,OCHCH$_2$N,J=8.2 Hz); 4.36 (q, 4H,OCH$_2$CH$_3$,J=7.1 Hz); 4.04(m,1H,CH); 3.70(t, 1H,OCHCHN,J=8.7 Hz); 3.28(t,1H,OCHCHN,J=8.2 Hz); 2.61(m,2H, CH$_2$); 1.78(m,2H,CH$_2$); 1.34(t,6H,OCH$_2$CH$_3$, J=7.1 Hz); 1.16(d, 3H, CH$_3$,J=6.8 Hz).

To 0.32 g of the (R,S) oxazolidinone diester is added, under argon, 6 ml of 2.5N sodium hydroxide. The reaction mixture is heated at reflux temperature for 20 hours, evaporated in vacuo and the residue is treated with ethyl alcohol. The formed solids are collected, washed with ethyl alcohol and diethyl ether, and air dried briefly. The solids are dissolved in water and purified by chromatography (40g of XAD-4 resin: previously washed with 200 ml of 1:1 water::methyl alcohol followed by 200 ml of water). The column is eluted with 100 ml of water followed by 100 ml of methyl alcohol. The methyl alcohol fractions containing the Rf 0.08 component (reverse phase tlc plates: water/methyl alcohol 7/1) are combined and evaporated in vacuo. The residue is triturated with alcohol and the formed solids are collected, rinsed with ethyl alcohol and diethyl ether and air dried to give 0.152 g of the desired product.

$^1$HNMR (D$_{20}$): δ7.40(m,3H,Ar); 7.26(m, 1H,Ar); 6.84(m, 2H,Ar); 6.73(m, 1H,Ar); 4.76(m, 1H); 2.90(m,2H); 2.79 (m, 1H); 2.6(m, 1H); 2.54 (m, 1H); 1.77 (m, 1H); 1.65(m, 1H), 1.11(d,3H,CH$_3$,J=6.3 Hz).

EXAMPLE 3

Disodium (R,R)-5-((3-(2-(3-chlorophenyl)-2-hydroxyethyl)amino)butyl)- 1,3-benzodioxole-2,2-dicarboxylate The title compound is prepared by the procedure of Example 2 using 0.76 g of the (R,R) isomer from Example 1 to give 0.111 g of the desired product.

Diethyl ester:

$^1$HNMR (CDCl$_3$): δ7.36(m,2H,Ar); 7.25(m,1H,Ar); 7.17(d, 1H,Ar); 6.81(d,1H,Ar,J=8.0 Hz); 6.69(d,1H,Ar,J=1.3 Hz); 6.61(dd,1H,Ar,J=8.0, 1.2 Hz); 5.49(dd,1H, OCHCH$_2$N,J= 8.7, 6.3 Hz); 4.35(q,4H,OCH$_2$CH$_3$,J=7.1 Hz); 4.01(m,1H, CH); 3.91(t,1H,OCHCHN,J=8.8 Hz); 3.28(dd,1H, OCHCHN,J=8.7, 6.4 Hz); 2.46(m,2H,CH$_2$); 1.69(m,2H, CH$_2$); 1.33(t,6H, OCH$_2$CH$_3$,J=7.1 Hz ); 1.21 ( d, 3 H, CH$_3$,J=6.9 Hz ).

Disodium salt:

$^1$HNMR (D$_2$): δ7.39(m.3H,Ar); 7.29(m,1H,Ar); 6.83(m, 2H,Ar); 6.69(dd,1H,Ar,J=8.0, 1.7 Hz); 2.95(m,2H); 2.82(m, 1H); 2.59(m,2H); 1.80 (m,1H); 1.68 (m,1H); 1.13(d,3H, CH$_3$,J=6.3 Hz).

EXAMPLE 4

Disodium 5-(2(2,5-dimethoxyphenyl)-1-hydroxyprop-2-yl)amino)propyl-1,3-benzodioxole-2,2-dicarboxylate One equivalent of 2-amino-1-(2,5-dimethoxyphenyl)propanol-1 is heated at reflux with one equivalent of 3,4-dibenzyloxyphenylacetone in toluene, and water is removed by azeotropic distillation. The reaction solution is evaporated in vacuo and the resulting imine is reduced with sodium borohydride in ethyl alcohol to give 2-[(1-(3,4-dibenzyloxyphenyl)prop-2-yl)amino]-1 -(2,5-dimethoxyphenyl)propanol-1. This product is then acetylated with acetic anhydride in pyridine to give the N-acetyl derivative; this N-acetyl derivative is catalytically debenzylated with 10% palladium on carbon in ethyl alcohol. The resultant catechol is reacted with diethyl dibromomalonate in acetonitrile in the presence of powdered potassium carbonate to give diethyl 5-(2-(1-(2,5-dimethoxyphenyl)-1-hydroxyprop-2 -yl)amino)propyl-1,3-benzodioxole-2,2-dicarboxylate. The diastereomers are separated by chromatography and each diester is hydrolyzed with sodium hydroxide in ethyl alcohol to give each diastereomer of disodium 5-(2-(1-(2,5-dimethoxyphenyl)-1-hydroxyprop-2-yl)amino)propyl-1,3 -benzodioxole-2,2-dicarboxylate.

EXAMPLE 5

(5-(2-((2-(3,Chlorophenyl)-2-hydroxyethyl)amino)propyl)-2,2-di(hydroxymethylcarbonyl)-1,3 -benzodioxole disodium salt One equivalent of 5-(3-chlorophenyl)-3-(2-(3,4-dihydroxyphenyl)-1 -methylethyl)-2-oxazolidinone, prepared by the procedure of U.S. Pat. No. 5,061,727, Example 1, is combined with 1.1 equivalents of 3,3-dibromo-2,4-pentanedione and 2.2 equivalents of powdered potassium carbonate in acetonitrile. The reaction mixture is stirred at room temperature for 48 hours, evaporated in vacuo and partitioned between methylene chloride and water. The organic layer is dried, filtered and evaporated in vacuo to give 5-(2-((2-(3-chlorophenyl)-2-hydroxyethyl)amino)propyl)-2, 2-diacetyl-1,3-benzodioxole.

One equivalent of the above product is stirred with two equivalent of trimethylsilyl chloride in tetrahydrofuran and triethylamine to give the his enol silyl ether. The his enol silyl ether is reacted with two equivalents of m-chloroperoxybenzoic acid in methylene chloride to give the his epoxide. The his epoxide is stirred in a solution of sulfuric acid, water and dioxane for 5 hours to give the bis hydroxymethyl ketone. This product is refluxed for 18 hours in excess 2.5N sodium hydroxide to give, after chromatography, (5-(2-((2-(3-chlorophenyl)-2-hydroxyethyl)amino-)propyl)-2,2 -di(hydroxymethylcarbonyl)-1,3-benzodioxole, disodium salt.

EXAMPLE 6

2- and 3- Chloromethyl-6-(2-(5-(3-chlorophenyl)-2-oxo-3 -oxazolidinyl)propyl)-1,4-benzodioxane One equivalent of 5-(3-chlorophenyl)-3-(2-(3,4-dihydroxyphenyl)-1-methylethyl)-2-oxazolidinone, prepared by the procedure of U.S. Pat. No. 5,061,727, Example 1, is combined with two equivalents of 2N sodium methoxide in methyl alcohol and the resulting slurry is stirred at room temperature for 30 minutes. One equivalent of 1,2-dibromo-3-chloropropane is added and the stirring is continued at room temperature for 24 hours. The solvent is evaporated in vacuo and the residue is dissolved in methylene chloride. The organic layer is dried, filtered through a pad of hydrous magnesium silicate and the filtrate is evaporated in vacuo to give 2-and 3- chloromethyl-6-(2-(5-(3-chloro-phenyl)-2-oxo-3 -oxazolidinyl)propyl)-1,4-benzodioxane. The individual, 2- and 3- isomers, are separated by chromatography.

EXAMPLE 7

[6-(2-(5-(3-Chlorophenyl)-2-hydroxethyl)amino) propyl)-phenyl)-2-methanesulfonyl-1,4 -benzodioxane One equivalent of product from Example 6, 2-isomer, and 2 equivalents of potassium hydrosulfide in dimethylsulfoxide is heated at 60° C. for 8 hours. The reaction mixture is poured into water, the precipitated product is collected and recrystallized from ethyl alcohol to give 6-(2-(5-(3-chlorophenyl)-2-oxo-3-oxazolidinyl)propyl)-1,4-benzodioxan-2-yl-thiomethanol.

One equivalent of the above thiomethanol derivative and 6 equivalents of 70% hydrogen peroxide in acetic acid is heated at 70° C. for 8 hours. Evaporation of the solvent gives the sulfonic acid, which is subsequently heated, at reflux temperature, with excess 2.5N sodium hydroxide and ethyl alcohol for 18 hours to give sodium [6-(2-(5-(3-chlorophenyl)-2-hydroxyethyl)-amino)propyl)-2-methanesulfonyl-1,4 -benzodioxande upon separation by ion exchange resin.

EXAMPLE 8

1-[6-(2-(5-(3-Chlorophenyl)-2-hydroxyethylamino)-propyl)-1,4-benzodioxan- 3-yl]dimethylsulfoxide One equivalent of product from Example 6, 3-isomer, and 2 equivalents of sodium methyl mercaptide in dimethylformamide, containing a catalytic amount of potassium iodide, is stirred at 60° C. for 18 hours. The mixture is poured into water, the resulting product is collected and recrystallized from ethyl alcohol to give 6-(2-(5-(3-chlorophenyl)-2-oxo-3-oxazolidinyl)propyl)-3-methylthiomethyl-1,4-benzodioxane.

The above thioether is combined with one equivalent of m-chloroperoxybenzoic acid in methylene chloride and stirred at room temperature for 18 hours. The reaction mixture is filtered. The filtrate is washed with sodium bicarbonate, dried and evaporated in vacuo to give the sulfoxide. The sulfoxide is heated at reflux temperature with 2.5N sodium hydroxide in ethyl alcohol to give methyl [6-(2-(5-(3-chlorophenyl)-2-hydroxyethyl)amino)propyl)-1,4 -benzodioxan-3-yl]methyl sulfoxide.

EXAMPLE 9

[2- and 3-[6(2-(5-(3-Chlorophenyl)-2-oxo-3- oxazolidinonyl)propyl)-4-benzodioxan]yl]acetonitrile One equivalent of product from Example 6 is stirred, at room temperature, with one equivalent of potassium cyanide in dimethylformamide, containing 0.01 equivalents of potassium iodide, for 48 hours. The solvent is evaporated in vacuo and the residue partitioned between water and methylene chloride. The organic layer is dried, passed through a pad of hydrous magnesium silicate and evaporated in vacuo to give the desired nitrile.

EXAMPLE 10

Sodium [2- and 3-[6-(2-(2-(3-chlorophenyl)-2-hydroxyethyl)amino)propyl)-1,4-benzodioxan ]yl]acetate The product of Example 9 is treated with 5N sodium hydroxide and heated, under argon, at reflux temperature for 18 hours. The reaction mixture is cooled and evaporated in vacuo. The residue is purified by chromatography (XAD-4 resin; water, followed by methyl alcohol) to give the desired product.

EXAMPLE 11

(R,R) 1,2-Dihydro-5-[2-(1-(3-chlorophenyl)-1 -hydroxyeth-2-ylamino)propyl]indene-2,2-dicarboxylate A mixture of one equivalent of diethyl 4-methylphthalate, two equivalents of N-bromosuccinimide and carbon tetrachloride is irradiated with a 500 W tungsten lamp for three hours. The mixture is filtered and the solution is shaken with excess sodium carbonate solution. Evaporation of the organic phase gives diethyl 4-formylphthalate. This aldehyde is combined with excess nitroethane, toluene and a catalytic amount of benzyl amine. The mixture is heated on a steam bath for 48 hours and evaporated in vacuo to give diethy 4-(2-nitropropen-1-yl)phthalate.

The above compound is treated with ten equivalents of lithium aluminum hydride in ether; followed by hydrolysis with sodium hydroxide to give 2-amino-1-[3,4-di(hydroxymethyl)]phenylpropane.

The amine is reacted with (−)-(R)-m-chlorostyrene oxide to give 1-(3-chlorophenyl)-2-[1-(3,4-di(hydroxymethyl)phenyl-2-propyl]aminoethanol. This compound is acetylated with acetic anhydride/pyridine and the acetylated product is treated with methanolic ammonia at 10° C. for 24 hours. Evaporation of the solvent gives the N-acetyl derivative.

The N-acetyl derivative is dissolved in pyridine and treated with two equivalents of methanesulfonyl chloride. The reaction is stirred at room temperature for 24 hours, evaporated and the residue is dissolved in methylene chloride. The organic layer is washed with cold water, dried and evaporated in vacuo to give N-acetyl-1-(3-chlorophenyl)-2 [1-(3,4-di(methanesulfonyloxymethyl)phenyl- 2-propyl] aminoethanol.

The above product and one equivalent of diethylmalonate are dissolved in tetrahydrofuran and 2 equivalents of sodium methoxide is added with stirring over 2 hours. The reaction mixture is stirred at room temperature for 24 hours, evaporated in vacuo, and the residue is combined with water and dilute acetic acid. The mixture is extracted with methylene chloride. The organic layers are dried, and evaporated in vacuo to give diethyl-(R,R) and diethyl-(R,S)-N-acetyl-1,2- dihydro-5-[2-(1-(3-chlorophenyl)-1-hydroxyeth-2-yl-amino)propyl]indene-2,2-dicarboxylate. The diastereomers are separated by chromatography to give the individual enantiomers. Hydrolysis of each separate enentiomer with 2.5N sodium hydroxide in ethyl alcohol gives disodium (R,R) and (R,S) 1,2-dihydro-5-[2-(1-(3-chlorophenyl)-1-hydroxyeth-2-yl-amino)propyl]indene-2,2-dicarboxylate.

EXAMPLE 12

7-(2-(2-(3-Chlorophenyl)-2-hydroxyethyl)amino)propyl)-1,5-dioxabenzocycloheptan-3-ol One equivalent of 5-(3-chlorophenyl)-3-(2-(3,4-dihydroxyphenyl)-1-methylethyl)-2-oxazolidinone, prepared by the procedure of U.S. Pat. No. 5,061,727 Example 1, is treated with one equivalent of 1,3-dibromoacetone and excess potassium carbonate in acetonitrile. The mixture is stirred at room temperature for 18 hours, filtered and evaporated in vacuo to give 7-(2-(5-(3-chlorophenyl)-2-oxo-3-oxazolidinyl)propyl)-1,5 -dioxabenzocycloheptan-3-one. One equivalent of this ketone is reduced, at room temperature for one hour, with excess sodium borohydride in methyl alcohol. The reaction mixture is poured into water, made acidic with 1N hydrochloric acid and extracted with methylene chloride. The organic extracts are dried and evaporated in vacuo to give 7-(2-(5-(3-chlorophenyl)-2-oxo-3-oxazolidinyl)propyl-1,5-dioxabenzocycloheptan-3-ol. Hydrolysis with 2.5N sodium hydroxide gives the title compound.

EXAMPLE 13

Sodium [7-(2-(2-(2-(3-chlorophenyl)-2-hydroxyethyl)amino)propyl-1,5-dioxebenzocycloheptan- 3-oxy]acetate One equivalent of the above alcohol is treated with 1.1 equivalents of sodium hydride in tetrahydrofuran and stirred at 60° C. for 1 hour. The reaction mixture is cooled to 15° C., 1.4 equivalents of methyl bromoacetate is added and the reaction is stirred at room temperature for 18 hours. The solvent is evaporated in vacuo and the residue is partitioned between water and methylene chloride. The organic layer is dried, and evaporated in vacuo to give methyl 7-(2-(5-(3-chlorophenyl)-2-oxo-3-oxazolidinyl)propyl-1,5-dioxabenzocycloheptan-3-yloxyacetate. Hydrolysis with 2.5N sodium hydroxide in ethyl alcohol, followed by chromatography on ion exchange resin gives the title compound.

EXAMPLE 14

Diethyl 5-[[2-(3-chlorophenyl)-2-hydroxy]ethylamino]-methylbenzimidazoline-2,2, -dicarboxylate dihydrochloride One equivalent of 3,4-dinitrotoluene and 2 equivalents of N-bromosuccinimide in carbon tetrachloride is irradiated with a 500 W tungsten lamp for 4 hours. The mixture is filtered and the filtrated is shaken with a solution of aqueous potassium carbonate. The organic layer is evaporated in vacuo to give 3,4-dinitrobenzaldehyde.

A solution of one equivalent of the above product and one equivalent of 2-amino-1-(3-chlorophenyl)ethanol in methanol is stirred with one equivalent of sodium borohydride to give 1-(3-chlorophenyl)-2-(3,4-dinitrophenyl)methylaminoethanol.

The above compound is dissolved in 5N hydrochloric acid and 10 equivalents of powdered iron is added over one hour as the mixture is stirred at 80° C.. The reaction is stirred until all the iron is consumed. The solution is made basic with sodium hydroxide and the two-phase mixture is extracted with methylene chloride. The organic layer is evaporated in vacuo to give 1-(3-chlorophenyyl)-2-(3,4-diaminophenyl-)methylaminoethanol.

The above phenylenediamine derivative is treated with one equivalent of diethyl dibromomalonate and 4 equivalents of anhydrous potassium carbonate in acetonitrile. The reaction is stirred for 18 hours at room temperature, filtered and evaporated in vacuo. The residue is dissolved in ethyl alcohol and hydrogen chloride gas is bubbled through. Cooling in ice causes the crystallization of diethyl 5-[[2-(m-chlorophenyl)2-hydroxy]ethylamino]methylbenzimidazoline-2,2 -dicarboxylate dihydrochloride.

EXAMPLE 15

5-(2-((2-(3-Chlorophenyl)-2-hydroxyethyl)amino)propyl-2,2-(ditetrazol-5-yl)-1,3 -benzodioxole, disodium salt One equivalent of 5-(3-chlorophenyl) -3-(2-(3,4-dihydroxyphenyl)-1-methylethyl )-2 -oxazolidinone, prepared by the procedure of U.S. Pat. No. 5,061,727; Example 1, one equivalent of dibromomalonamide, acetonitrile, and 4 equivalents of potassium carbonate are stirred at room temperature for 18 hours. The reaction mixture is filtered and evaporated in vacuo to give 5-(2-(5-(3-chlorophenyl)-2-oxo-3-oxazolidinyl)propyl)-1,3 -benzodioxole-2,2-dicarboxamide.

The bis-amide is stirred, for 8 hours at 80° C., with 2 equivalents of phosphorus oxychloride. The solution is poured onto ice and the precipitated product is extracted with methylene chloride. The organic layer is washed with a solution of sodium bicarbonate, dried, filtered through a pad of hydrous magnesium silicate and evaporated in vacuo to give 5-(2-(5-(3-chlorophenyl)-2-oxo-3-oxazolidinyl)propyl)-1,3-benzodioxole-2,2-dicarbonitrile.

The above product, dissolved in toluene, is heated at reflux temperature with 4 equivalents of tri-(n-butyl)tin chloride and 4 equivalent of sodium azide for 24 hours. The solution is filtered and cooled to 0° C. A small amount of methyl alcohol is added and hydrogen chloride gas is bubbled into the solution for 15 minutes while maintaining the temperature at 0°–10° C. The solid product is collected by filtration and then refluxed for 24 hours in 2.5N sodium hydroxide in ethyl alcohol. Purification by ion exchange column gives 5-(2-((2-(3-chlorophenyl)-2-hydroxyethyl)amino)propyl-2,2-(ditetrazol-5-yl)-1,3-benzodioxole, disodium salt.

EXAMPLE 16

Diethyl (R,R)-1,2-dihydro-5[2-(1-(3-chlorophenyl)-1-hydroxyeth-2-ylamino)propyl] indene-2,2-dicarboxylate dihydrochloride One equivalent of the (R,R) disodium salt product from Example 11 is dissolved in anhydrous ethyl alcohol, and hydrogen chloride gas is bubbled through the solution. The mixture is stirred at room temperature for 24 hours. Sodium chloride is removed by filtration and the filtrate is evaporated in vacuo to give the title compound.

EXAMPLE 17

(R,R)-1,2-Dihydro-5-[2-(1-(3-chlorophenyl)-1-hydroxyeth-2-ylamino)propyl] indene-2,2-di(N-glycyl)-carboxamidedisodium salt The product from Example 16 is combined with 3.1 equivalents of triethylamine and 2 equivalents of glycine t-butyl ester in ethyl alcohol. The reaction mixture is heated at reflux temperature for 6 hours, evaporated in vacuo, and the residue partitioned between water and ethyl acetate. The organic layer is evaporated in vacuo to give (R,R)-1,2-dihydro-5-[2-(1-(3-chlorophenyl)-1-hydroxyeth-2-ylamino)propyl]indene-2,2-di(N-glycyl)carboxamide di(t-butyl)ester.

The above compound is dissolved in ethyl alcohol and excess 2N hydrochloric acid is added and the resulting mixture is stirred at room temperature for 2 hours. The solution is adjusted to pH 10 with sodium hydroxide, evaporated in vacuo and the residue is purified by ion exchange chromatography to give the title compound.

EXAMPLE 18

Diethyl (R,R)-5-((3-(2-(3-chlorophenyl)-2-hydroxyethyl)amino)butyl-1,3-benzodioxole-2,2-dicarboxylate hydrochloride The title compound is prepared by the procedure of Example 16 using the product from Example 3.

Substantially following the methods described in detail hereinabove in Example 16 and using the appropriate alcohol, the compounds of this invention listed below in Examples 19 and 20 are prepared.

EXAMPLE 19

Diisopropyl (R,R)-5-((3-(2-(3-chlorophenyl)-2-hydroxyethyl)amino)butyl-1,3-benzodioxole- 2,2-dicarboxylate hydrochloride filtrate is evaporated in vacuo. The residue is recrystallized from acetone to give the title compound.

EXAMPLE 22

(R,R)-5-((3-(2-(3-Chlorophenyl)-2-hydroxyethyl)amino)butyl)-1,3-benzodioxole-2,2-di(N-(2-methoxyethyl))carboxamide tartrate The product from Example 18 is combined with one equivalent of ethyldiisopropylamine and 2 equivalents of 2-methoxyethylamine in ethyl alcohol. The reaction mixture is stirred at room temperature for 24 hours, washed with cold saturated sodium chloride, dried, and evaporated in vacuo. The residue is combined with one equivalent of tartaric acid in ethyl alcohol to give the title compound.

Substantially following the methods described in detail hereinabove in Example 22 and using the appropriate amine, the compounds of this invention listed below in Examples 23–34 are prepared.

TABLE 1

| Example | Amine | Product |
|---|---|---|
| 23 | D(+)-glucosamine | (R,R)-5-((3-(2-(3-Chlorophenyl)-2-hydroxyethyl)amino)butyl)-1,3-benzodioxole-2,2-di(N-(2-deoxyglucos-2-yl))carboxamide |
| 24 | 3-aminomethyl-pyridine | (R,R)-5-((3-(2-(3-Chlorophenyl)-2-hydroxyethyl)amino)butyl)-1,3-benzodioxole-2,2-di(N-(3-pyridylmethyl))carboxamide |
| 25 | 3-aminopyrazole | (R,R)-5-((3-(2-(3-Chlorophenyl)-2-hydroxyethyl)amino)butyl)-1,3-benzodioxole-2,2-di(N-(3-pyrazolyl))carboxamide |
| 26 | 2-aminoimidazole | (R,R)-5-((3-(2-(3-Chlorophenyl)-2-hydroxyethyl)amino)butyl)-1,3-benzodioxole-2,2-di(N-(2-imidazolyl))carboxamide |
| 27 | 5-amino-3-methyl-isothiazole | (R,R)-5-((3-(2-(3-Chlorophenyl)-2-hydroxyethyl)amino)butyl)-1,3-benzodioxole-2,2-di(N-(3-methylisothiazol-5-yl))carboxamide |
| 28 | 3-amino-5-methyl-isoxazole | (R,R)-5-((3-(2-(3-Chlorophenyl)-2-hydroxyethyl)amino)butyl)-1,3-benzodioxole-2,2-di(N-(5-methylisoxazol-3-yl))carboxamide |
| 29 | 5-aminotetrazole | (R,R)-5-((3-(2-(3-Chlorophenyl)-2-hydroxyethyl)amino)butyl)-1,3-benzodioxole-2,2-di(N-(5-tetrazolyl))carboxamide |
| 30 | 2-aminothiazole | (R,R)-5-((3-(2-(3-Chlorophenyl)-2-hydroxyethyl)amino)butyl)-1,3-benzodioxole-2,2-di(N-(2-thiazolyl))carboxamide |
| 31 | 3-amino-1,2,4-triazine | (R,R)-5-((3-(2-(3-Chlorophenyl)-2-hydroxyethyl)amino)butyl)-1,3-benzodioxole-2,2-di(N-(1,2,4-triazin-3-yl))carboxamide |
| 32 | 3-amino-1,2,4-triazole | (R,R)-5-((3-(2-(3-Chlorophenyl)-2-hydroxyethyl)amino)butyl)-1,3-benzodioxole-2,2-di(N-(1,2,4-triazol-3-yl))carboxamide |
| 33 | furfurylamine | (R,R)-5-((3-(2-(3-Chlorophenyl)-2-hydroxyethyl)amino)butyl)-1,3-benzodioxole-2,2-di(N-(furfuryl))carboxamide |
| 34 | 3-aminothiophene | (R,R)-5-((3-(2-(3-Chlorophenyl)-2-hydroxyethyl)amino)butyl)-1,3-benzodioxole-2,2-di(N-(3-thienyl))carboxamide |

EXAMPLE 20

Dimethyl (R,R)-5-((3-(2-(3-chlorophenyl)-2-hydroxyethyl)amino)butyl-1,3-benzodioxole- 2,2-dicarboxylate hydrochloride

EXAMPLE 21

(R,R)-5-(3-(2-(3-Chlorophenyl)-2-hydroxyethyl)-)amino)butyl-1,3-benzodioxole-2,2-dicarboxylic acid phenylmethylenedioxy diester hydrochloride The product from Example 3 is combined with 3 equivalents of benzaldehyde in benzene and hydrogen chloride gas is bubbled through this solution. The mixture is stirred for 24 hours, the formed sodium chloride is collected and the

EXAMPLE 35

R*,S*) and (R*,R*)-5-(3-Trifluoromethylphenyl)-3-[(3-4-dimethoxyphenyl)-butan-2-yl]oxazolidinone The title compound is prepared by the procedure of Example 1 using m-trifluoromethylstyrene oxide.

EXAMPLE 36

Disodium (R*,S*) and (R*,R*)-5-(3-Trifluoromethylphenyl)-2-hydroxyethyl)amino)butyl)-1,3-benzodioxole-2,2-dicaboxylate The title compound is prepared by the procedures of Examples 2 and 3 using the product of Example 35.

EXAMPLE 37

Diisopropyl 5-(2-amino)propyl-1,3-benzodioxole-2,2-dicarboxylate one equivalent of (R)-1-(3,4-dimethoxyphenyl)-2-aminopropane is combined with one equivalent of 2,2,2-trichloroethyl chloroformate in methylene chloride and sodium hydroxide solution. The resulting mixture is stirred at room temperature for 6 hours. The layers are separated, the organic layer is washed with dilute hydrochloric acid, dried and evaporated to give the desired urethane.

The above urethane is dissolved in methylene chloride, and then one equivalent of boron tribromide is added and this mixture is stirred at 0°–5° C. for 15 minutes, then at room temperature for 20 minutes. The reaction is quenched with water, the organic layer is dried and evaporated to give (R)-1-(3,4-dihydroxyphenyl)-2-(2,2,2-trichloroethoxycarbonyl)amino propane.

The above catechol is combined with one equivalent of diisopropyl dibromomalonate in acetone and powdered, anhydrous potassium carbonate. The reaction mixture is stirred at room temperature for 18 hours. Filtration and evaporation of the solution gives diisopropyl 5-((2,2,2-trichloroethoxycarbonyl)amino)propyl-1,3-benzodioxole-2,2-dicarboxylate.

This diester is stirred in a mixture of powdered zinc in acetic acid/tetrahydrofuran/water for 6 hours at room temperature. The mixture is filtered, and the filtrate is neutralized with sodium bicarbonate. Isolation of the product gives diisopropyl 5- (2-amino) propyl-1,3-benzodioxole-2,2-dicarboxylate.

$^1$H NMR (CDCl$_3$):delta 6.86(d,1H, J=8.0 Hz); 6.79(d,1H, J=1.3 Hz); 6.71(dd,1H, J=1.3 and 8.0 Hz); 5.19 (septet,2H, J=6.3 Hz); 3.07-3.13 (m,1H); 2.64(dd,1H, J=13.4 and 5.2 Hz); 2.44(dd,1H, J=13.4 and 8.1 Hz); 1.32(d,12H, J=6.3 Hz); 1.10(d,3H,J=6.3 Hz).

EXAMPLE 38

Diisopropyl 5-(2-(2-naphthyl)-2-hydroxyethyl)-amino)propyl)-1,3-benzodioxole-2,2-dicarboxylate hydrochloride A solution of one equivalent of (R)-diisopropyl 5-(2-amino) propyl-1,3-benzodioxole-2,2-dicarboxylate and one equivalent of (2-naphthyl)oxirane in ethanol is heated at reflux temperature for 8 hours. The solvent is evaporated in vacuo. The residue is dissolved in diethyl ether and hydrogen chloride gas is bubbled through the solution. The precipitate is recrystallized to give (R,R) and (S,R) 5-(2-((2-(2-naphthyl)-2-hydroxyethyl)amino)propyl)-1,3-benzodioxole-2,2-dicarboxylate hydrochloride.

EXAMPLE 39

Disodium 5-(2-(3-chlorophenyl)-2-hydroxyethyl)aminomethyl-1,3-benzodioxole- 2,2-dicarboxylate One equivalent of 3,4-dihydroxybenzaldehyde, 1.1 equivalents of diethyl dibromomalonate and powdered potassium carbonate is stirred in acetonitrile at room temperature for 18 hours. The reaction mixture is filtered, evaporated in vacuo, and distilled to give diethyl 5-formyl-1,3-benzodioxole-2,2-dicarboxylate.

$^1$H NMR (CDCl$_3$):delta 9.9(s,1H,CHO); 7.5(m,2H,aromatic); 7.1(d, 1H,aromatic); 4.45(q,4H,CH$_2$); 1.8 (t,6H, CH$_3$).

One equivalent of the above aldehyde, one equivalent of 2-amino-1-(3-chlorophenyl)ethanol, one equivalent of acetic acid, and 1.5 equivalents of sodium triacetoxyborohydride in 1,2-dichloroethane is stirred at room temperature for 1 hour. The solvent is evaporated in vacuo. The residue dissolved in 2.5N sodium hydroxide in ethyl alcohol, heated at reflux temperature for one hour, and evaporated in vacuo. The residue is passed through an ion exchange column to give the title compound.

EXAMPLE 40

(R,R) and (S,R)-5-(2-((2-(3-Trifluoromethoxyphenyl)-2-hydroxyethyl)amino)propyl-1,3-benzodioxole-2,2-dicarboxylate hydrochloride A solution of one mole equivalent of m-trifluoromethoxybenzaldehyde in dry tetrahydrofuran is combined with 5 mole equivalents of diiodomethane, 9 mole equivalents of zinc powder, 1 mole equivalent of titanium tetraisopropoxide, and the mixture is stirred at room temperature for 3 hours. The product is extracted from the mixture after removal of solvent in vacuo to give m-trifluoromethoxyphenylethene.

This compound is combined with one mole equivalent of m-chloroperoxybenzoic acid in methylene chloride, and the mixture is stirred at 0° C. for 24 hours. The reaction mixture is filtered, washed with sodium bicarbonate solution, dried and evaporated in vacuo to give m-trifluoromethoxy phenyl styrene oxide. This is combined with diisopropyl 5-(2-amino)propyl-1,3-benzodioxole-2,2-dicarboxylate as in Example 38 to give (R,R) and (S,R)-5-(2-((2-(trifluoromethoxyphenyl)-2-hydroxy-ethyl)amino)propyl)- 1,3-benzodioxole-2,2-dicarboxylate.

EXAMPLE 41

(R,R) and (S,R)-5-(2-((2-(3-Difluoromethoxyphenyl)-2-hydroxyethyl)amino)propyl- 1,3-benzodioxole-2,2-dicarboxylate hydrochloride By essentially employing the procedure of Example 40, and by the use of m-difluoromethoxybenzaldehyde, there is obtained (R,R) and (S,R)-5-(2-((2-(3-difluoromethoxyphenyl)-2-hydroxyethyl)amino)propyl)-1,3-benzodioxole-2,2-dicarboxylate.

We claim:

1. A compound of the formula:

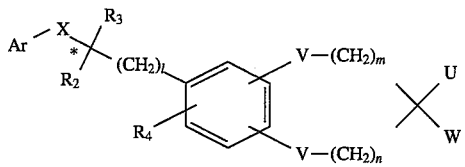

wherein:

Ar is naphth-(1 or 2)-yl which is substituted with hydrogen, straight or branched (C$_1$–C$_6$)alkyl, bromine, chlorine, fluorine, iodine, (C$_1$–C$_6$)alkoxy, difluoromethyl, trifluoromethyl, trifluoromethoxy, or difluoromethoxy, 1,2,3,4-tetrahydro-(5 or 6)-naphthyl which is substituted with hydrogen, straight or branched (C$_1$–C$_6$)alkyl, bromine, chlorine, fluorine, iodine, (C$_1$–C$_6$)alkoxy, difluoromethyl, or trifluoromethyl, indanyl, or

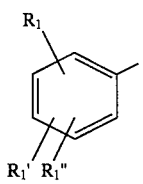

wherein $R_1$, $R_1'$, and $R_1''$ are independently straight or branched chain $(C_1-C_6)$alkyl, hydrogen, bromine, chlorine, fluorine, iodine, $(C_1-C_6)$alkoxy, difluoromethyl, trifluoromethyl, nitro, hydroxy,$(C_1-C_6)$hydroxyalkyl, —$NR_5R_6$ wherein $R_5$ and $R_6$ are independently hydrogen, straight and branched $(C_1-C_6)$alkyl, substituted phenyl, or substituted phenyl $(C_1-C_6)$alkyl, —$SR_7$, wherein $R_7$ is hydrogen or straight or branched $(C_1-C_6)$alkyl, carboxy or $(C_1-C_6)$alkoxycarbonyl;

$R_2$ and $R_3$ are hydrogen or $(C_1-C_4)$alkyl;

m and n are integers from 0–1;

l is an integer of 0, 2 or 3;

V is oxygen and each V is ortho to the other V;

W and U are independently hydrogen, hydroxy, —$CO_2R_8$ or — $OCH_2CO_2R_8$ wherein $R_8$ is hydrogen or straight or branched $(C_1-C_{10})$alkyl; —$CONR_9R_{10}$ or —$OCH_2CONR_9R_{10}$ wherein $R_9$ and $R_{10}$ are hydrogen, straight or branched $(C_1-C_{10})$alkyl, substituted benzyl, substituted phenyl, a heterocycle selected from the group consisting of pyridylmethyl, thienyl, furfuryl, furyl, pyrazolyl, imidazolyl, isothiazolyl, isoxazolyl, tetrazolyl, thiazolyl, 1,2,4-triazinyl and 1,2,4-triazolyl, a saccharide residue or a peptide; cyano, cyano$(C_1-C_6)$alkyl, chlorine, bromine, halo$(C_1-C_6)$alkyl, hydroxy$(C_1-C_6)$alkyl, hydroxymethylcarbonyl, SH, $SO_3H$, $S(O)CH_3$, $SO_2CH_3$, —$CH_2SO_3H$,— $CH_2SR_{11}$, —$CH_2S(O)R_{11}$ wherein $R_{11}$ is $(C_1-C_4)$alkyl, tetrazol-5-yl, or U and W taken together with the carbon atom to which they are attached are carbonyl;

X is a divalent radical:

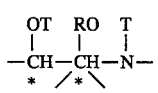

wherein $R_o$ is $(C_1-C_3)$alkyl;

T is hydrogen, $(C_1-C_4)$alkyl or $(C_1-C_4)$acyl;

and the pharmaceutically acceptable salts and esters, the enantiomers, the racemic mixtures and diastereomeric mixtures thereof.

2. A compound according to claim 1, wherein $R_1$ is hydrogen, chloro, or trifluoromethyl, and l is the integer 2.

3. A compound according to claim 2, wherein m and n are the integer 1, and U and W are carboxy or —$CO_2^-Na^+$.

4. A compound according to claim 2, wherein U and W are hydroxymethylcarbonyl.

5. An optically active compound according to claim 1, disodium (R,R)-5-(3-((2-(3-chlorophenyl)-2-hydroxyethyl)amino)butyl)-1,3-benzodioxole- 2,2-dicarboxylate.

6. A compound according to claim 1, disodium (R*,R*)-5-(2-(3-chlorophenyl)-2-hydroxyethyl)aminomethyl-1,3-benzodioxole-2,2-dicarboxylate.

7. An optically active compound according to claim 1, disodium 5-(2-(3-chlorophenyl)-2-hydroxyethyl)aminomethyl-1,3-benzodioxole-2,2-dicarboxylate.

8. The compound (R*,R*)-(5-(2-((2-(3-chlorophenyl)-2-hydroxyethyl)amino)propyl) -2,2 -di(hydroxymethylcarbonyl)-1,3-benzodioxole disodium salt.

9. A pharmaceutical composition for treating diabetes, hyperglycemia, or obesity in humans or other mammals, comprising an effective amount of a compound according to claim 1, in combination with a pharmaceutically acceptable carrier.

10. A pharmaceutical composition for treating inflammatory bowel disease, irritable bowel syndrome, non-specific diarrhea and dumping syndrome, depression, hyperlipidemia, hypertension, hyper- triglyceridemia, hypercholesterolemia, atherosclerosis, and conditions of low HDL (high density lipoprotein) in humans or other mammals, comprising an effective amount of a compound according to claim 1, in combination with a pharmaceutically acceptable carrier.

11. A pharmaceutical composition for treating diabetes, hyperglycemia, or obesity in humans or other mammals, comprising an effective amount of disodium (R,R)-5-(3-((2-(3-chlorophenyl)-2-hydroxyethyl)amino)butyl)-1,3-benzodioxole- 2,2-dicarboxylate and a pharmaceutically acceptable carrier.

12. A composition according to claim 11 in unit dosage form.

13. A composition according to claim 12 in the form of a tablet, a pill, a capsule, an ampule, and elixir, a suspension or a syrup.

14. A method of treating hyperglycemia in mammals which comprises administering to a hyperglycemic patient an antihyperglycemic effective amount of a compound of claim 1.

15. A method of treating diabetes in mammals which comprises administering to a diabetic patient an antidiabetic effective amount of a compound of claim 1.

16. A method of treating obesity in mammals which comprises administering to an obese patient an antiobesity effective amount of a compound of claim 1.

17. A method of increasing lean meat in edible animals which comprises administering to an animal an antilipogenic effective amount of a compound of claim 1.

* * * * *